US009505852B2

(12) United States Patent
Gagnon

(10) Patent No.: US 9,505,852 B2
(45) Date of Patent: Nov. 29, 2016

(54) N,N,N-TRIALKYLAMINOPOLYMERS, METHODS OF THEIR PREPARATION AND USES THEREOF

(75) Inventor: Jonathan Gagnon, Rimouski (CA)

(73) Assignee: RIVAL, SOCIÉTÉ EN COMMANDITE, Montreal (CA)

( * ) Notice: Subject to any disclaimer, the term of this patent is extended or adjusted under 35 U.S.C. 154(b) by 0 days.

(21) Appl. No.: 14/125,759

(22) PCT Filed: Jun. 13, 2012

(86) PCT No.: PCT/CA2012/050399
§ 371 (c)(1),
(2), (4) Date: Dec. 12, 2013

(87) PCT Pub. No.: WO2012/171125
PCT Pub. Date: Dec. 20, 2012

(65) Prior Publication Data
US 2014/0107329 A1    Apr. 17, 2014

Related U.S. Application Data

(60) Provisional application No. 61/496,225, filed on Jun. 13, 2011.

(51) Int. Cl.
    C08B 37/00     (2006.01)
    A61Q 17/04     (2006.01)
    A61K 8/73      (2006.01)
    A61Q 19/00     (2006.01)
    A61K 31/722    (2006.01)
    C08B 37/08     (2006.01)

(52) U.S. Cl.
    CPC .......... *C08B 37/0063* (2013.01); *A61K 8/736* (2013.01); *A61K 31/722* (2013.01); *A61Q 17/04* (2013.01); *A61Q 19/00* (2013.01); *C08B 37/003* (2013.01)

(58) Field of Classification Search
    None
    See application file for complete search history.

(56) References Cited

U.S. PATENT DOCUMENTS

| | | |
|---|---|---|
| 5,744,166 A | 4/1998 | Illum |
| 6,207,197 B1 | 3/2001 | Illum |
| 6,328,967 B1 | 12/2001 | Rivera |
| 6,410,046 B1 | 6/2002 | Lerner |
| 6,726,920 B1 | 4/2004 | Theeuwes et al. |
| 7,282,194 B2 | 10/2007 | Sung et al. |
| 7,291,598 B2 | 11/2007 | Sung et al. |
| 7,381,716 B2 | 6/2008 | Sung et al. |
| 7,393,666 B2 | 7/2008 | Tamm et al. |
| 7,407,943 B2 | 8/2008 | Crooke et al. |
| 7,427,470 B2 | 9/2008 | Ward et al. |
| 7,455,830 B2 | 11/2008 | Sung et al. |
| 2010/0249390 A1 | 9/2010 | Azuma et al. |

FOREIGN PATENT DOCUMENTS

| | | |
|---|---|---|
| CA | 2507846 A1 | 6/2003 |
| CA | 2507870 A1 | 7/2003 |
| CA | 2580460 A1 | 3/2006 |
| CA | 2623475 A1 | 4/2007 |
| CA | 2631891 A1 | 6/2007 |
| CN | 101157735 A | 4/2008 |
| EP | 1250118 B1 | 10/2002 |
| JP | 2002-037801 A | 2/2002 |
| JP | 2010-242020 A1 | 10/2010 |
| WO | 00/55210 A1 | 9/2000 |
| WO | 03/029329 A2 | 4/2003 |

OTHER PUBLICATIONS

Mainz, Basic Practical NMR Concepts: A Guide for the modern Laboratory, 2004).*
Rúnarsson, Carbohydrate Polymers 74 (2008) 740-744.*
Terpstra AH, Holmes JC, Nicolosi RJ. 1991. The hypocholesterolemic effect of dietary soybean protein vs. casein in hamsters fed cholesterol-free or cholesterol-enriched semipurified diets. J Nutr 121: 944-7.
Thanou M., Florea B.I., Langemeyer M.W.E., Verhoef J.C., Junginger H.E., "N-trimethylated chitosan chloride (TMC) improves the intestinal permeation of the peptide drug buserelin in vitro (Caco-2 cells) and in vivo (Rats)", Pharm. Res., 2000, 17, 27.
Thanou M., Kotze A.F., Scharringhausen T., Leuben H.L., De Boer A.G., Verhoef J.C., Junginger H.E., J. "Effect of degree of quaternization of N-trimethyl chitosan chloride for enhanced transport of hydrophilic compounds across intestinal Caco-2 cell nonolayers", Controlled Release, 2000, 64, 15.
Thanou M., Verhoef J.C., Junginger H.E., "Oral drug absorption enhancement by chitosan and its derivatives" Adv. Drug Delivery Rev., 2001, 52, 117.
Thanou M., Verhoef J.C., Verheijden J.H.M., Junginger H.E., "Intestinal absorption of octreotide using trimethyl chitosan chloride: studies in pigs", Pharm. Res., 2001, 18, 823.
Thanou, M. et al. "Effect of N-trimethyl chitosan chloride, a novel absorption enhancer, on caco-2 intestinal epithelia and the ciliary beat frequency of chicken embryo trachea," Int. J. Pharm. Aug. 5, 1999;185(1):73-82.

(Continued)

*Primary Examiner* — Layla Berry
(74) *Attorney, Agent, or Firm* — Isabelle Pelletier

(57) ABSTRACT

There is provided a method for the preparation of an N,N,N-trialkylaminopolymer having one or more unsubstituted heteroatoms different from nitrogen atom. The method comprises a first step of alkylating an aminopolymer to produce an N,N-dialkylaminopolymer, wherein substantially no N,N,N-trialkylaminopolymer is produced; and a second step of alkylating the N,N-diaminopolymer to produce the N,N,N-trialkylaminopolymer. The N,N,N-trialkylaminopolymer is produced with a satisfactory degree of quaternization and with only a low percentage of the unsubstituted heteroatoms alkylated. The N,N,N-trialkylaminopolymer can be an N,N,N-trialkylaminopolysaccharide or an N,N,N-trialkylchitosan such as N,N,N-trimethylchitosan.

19 Claims, 7 Drawing Sheets

(56) References Cited

OTHER PUBLICATIONS

Thanou, M. et al. "Intestinal absorption of octreotide: N-trimethyl chitosan chloride (TMC) ameliorates the permeability and absorption properties of the somatostatin analogue in vitro and in vivo," J. Pharm. Sci. Jul. 2000;89(7):951-7.
Ueno, H. "Topical formulations and wound healing applications of chitosan", Adv. Drug Deliv. Rev., 2001, 52, 105-115.
Verheul, R.J., "Synthesis, characterization and in vitro biological properties of O-methyl free N,N,N-trimethylated chitosan", Biomaterials, 2008, 29, 3642-3649.
Verheul, R.J. , Ph.D., "Tailorable Trimethyl Chitosans as Adjuvant for Intranasal Immunization", 2010, Universiteit Utrecht, 205 pages, ISBN 978-90-39354292.
Wilson TA, Nicolosi RJ, Rogers EJ, Sacchiero R, Goldberg DJ. 1998. Studies of cholesterol and bile acid metabolism, and early atherogenesis in hamsters fed GT16-239, a novel bile acid sequestrant (BAS). Atherosclerosis 140: 315-24.
Wing L., Jordan L.P., "Cationic cellulosic polymers with multifunctional and outstanding performance for personal care", www.dow.com, on May 19, 2010.
Xu T., Xin M., Li M., Huang H., Zhou S., "Synthesis, characteristics and antibacterial activity of N,N,N,-trimethyl chitosan and its carboxymethyl derivatives", Carbohydr. Polym., 2010, 81, 931-936.
International Search Report issued in PCT/CA12/050399 issued on Jul. 16, 2012.
Avadi M.R., Zohuriaan-Mehr M.J., Younessi P., Amini M., Rafiee Tehrani M., Shafiee A., "Optimized Synthesis and Characterization of N-Triethyl Chitosan", J. Bioact. Compat. Polym., 2003, 18, 469.
Bayat A., Sadeghi A.M.M., Avadi M.R., Amini M., Rafiee-Tehrani M., Shafiee A., Majlesi R., Junginger H.E., "Synthesis of N,N-dimethyl N-ethyl Chitosan as a Carrier for Oral Delivery of Peptide Drugs", J. Bioact. Compat. Polym., 2006, 21, 433.
Beynen AC, West CE, Van Raaij JM, Katan MB. 1984. Dietary soybean protein and serum cholesterol. Am J Clin Nutr 39: 840-1.
Beynen AC. 1990. Comparison of the mechanisms proposed to explain the hypocholesterolemic effect of soybean protein versus casein in experimental animals. J Nutr Sci Vitaminol (Tokyo) 36 Suppl 2: S87-93.
Borchard G., "Chitosan for gene delivery", Adv. Drug Delivery Rev., 2001, 52, 145.
Britto D., Assis B.G.O., "A novel method for obtaining a quaternary salt of chitosan", Carbohydr. Polym., 2007, 69, 305.
Britto D., Assis B.G.O., "Synthesis and mechanical properties of quaternary salts of chitosan-based films for food application", Intl. J. Biol. Macromol., 2007, 41, 198.
Britto D., Campana-Filho S.P., "A kinetic study on the thermal degradation of N,N,N,-trimethylchitosan", Polym. Degrad. Stab., 2004, 84, 353.
Britto D., Forato L.A., Assis O.B.G., "Determination of the average degree of quatemization of N,N,N-trimethylchitosan by solid state 13C NMR", Carbohydr. Polym., 2008, 74, 86-91.
Cafaggi S., Russo E., Stefani R., Leardi R., Caviglioli G., Parodi B., Bignardi G., Totero D., Aiello C., Viale M., "Preparation and evaluation of nanoparticles made of chitosan or N-trimethyl chitosan and a cisplatin-alginate complex", J. Control. Release, 2007, 121, 110-123.
Clarke J., Robbins C.R., Reich C., "Influence of hair volume and texture on hair body of tresses", Journal of the society of cosmetic chemists, 1991, 42, 341.
Cumming J.L., Hawker D.W., Nugent K.W., Chapman H.F., "Ecotoxicities of polyquaterniums and their associated polyelectrolyte-surfactant aggregates (PSA) to Gambusia holbrooki", Journal of Environmental Science and Health Part A, 2008, 43, 113.
Curti E., Britto D., Campana-Filho S.P., "Methylation of chitosan with Iodomethane: Effect of Reaction Conditions on Chemoselectivity and Degree of Substitution", Macromol. Biosci., 2003, 3, 571-576.
Daggy BP, O'Connell NC, Jerdack GR, Stinson BA, Setchell KD. 1997. Additive hypocholesterolemic effect of psyllium and cholestyramine in the hamster: influence on fecal sterol and bile acid profiles. J Lipid Res 38: 491-502.
Di Colo G., Burgalassi S., Zambito Y., Monti D., Chetoni P., "Effects of Different N-trimethyl chitosans on in vitro/in vivo ofloxacin transcorneal permeation", J. Pharm. Sci., 2004, 93, 2851-2862.
Di Colo G., Y., Zaino C., "Polymeric enhancers of mucosal epithelia permeability: Synthesis, transepithelial penetration-enhancing properties, mechanism of action, safety issues", J. Pharm. Sci., 2008, 97, 1652-1680.
Dodane, V. et al. "Effect of chitosan on epithelial permeability and structure," Int. J. Pharm. May 10, 1999;182(1):21-32.
Dodou D., Breedveld P., Wieringa P.A., "Mucoadhesives in the gastrointestinal tract: revisiting the literature for novel applications", Euro. J. Pharm. Biopharm., 2005, 60, 1.
Drovetskaya T.V., Kreeger R.L., Amos J.L., Davis C.B., Zhou S., "Effects of low-level hydrophobic substitution on conditioning properties of cationic cellulosic polymers in shampoo systems", Journal of Cosmetic Science, 2004, 55 (Supplement), S195.
Dung P., Milas M., Rinaudo M., Desbrières J., "Water soluble derivatives obtained by controlled chemical modifications of chitosan", Carbohydr. Polym., 1994, 24, 209-214.
El-Sharif, A.A. et al. "Chitosan-EDTA New combination is a promising candidate for treatment of bacterial and fungal infections", Curr. Microbiol., 2011, 62, 739-745.
Fernandez ML, Wilson TA, Conde K, Vergara-Jimenez M, Nicolosi RJ. 1999. Hamsters and guinea pigs differ in their plasma lipoprotein cholesterol distribution when fed diets varying in animal protein, soluble fiber, or cholesterol content. J Nutr 129: 1323-32.
Florea B.I., Thanou M., Junginger H.E., Borchard G., "Enhancement of bronchial octreotide absorption by chitosan and N-trimethyl chitosan shows linear in vitro/in vivo correlation", J. Control. Release, 2006, 110, 353.
Gruber J.V., "Polyquaternium-10: cornerstone of a personal care revolution", Journal of Cosmetic Science, 2009, 60, 385.
Hamman J.H., Kotzé A.F., "Effect of the type of base and number of reaction steps on the degree of quaternization and molecular weight of N-trimethyl chitosan chloride", Drug Dev. Ind. Pharm., 2001, 27, 373-380.
Hamman J.H., Stander M., Junginger H.E., Kotze A.F., "Enhancement of paracellular drug transport across mucosal epithelia by N-trimethyl chitosan chloride", S. T. P. Pharma Sci., 2000, 10, 35.
Harding J.R., Jones J.R., Lu S.-Y., Wood R., "Development of a microwave-enhanced isotopic labelling procedure based on the Eschweiler-Clarke methylation reaction", Tetrahedron Lett., 2002, 43, 9487-9488.
Illum, L. et al. "Chitosan as a novel nasal delivery system for peptide drugs," Pharm. Res. Aug. 1994;11(8):1186-9.
Jia Z., Shen D., Xu W., "Synthesis and antibacterial activities of quaternary ammonium salt of chitosan", Carbohydr. Res., 2001, 333, 1.
Johansson J, Carlson LA. 1990. The effects of nicotinic acid treatment on high density lipoprotein particle size subclass levels in hyperlipidaemic subjects. Atherosclerosis 83: 207-16.
Kean T., Roth S., Thanou M., "Trimethylated chitosans as non-viral gene delivery vectors: Cytotoxicity and transfection efficiency", J. Control. Release, 2005, 103, 643.
Kenawy, E. et al. "The chemistry and applications of antimicrobial polymers: A state-of-the-art review", Biomacromolecules, 2007, 8, 1359-1384.
Kim C.H., Choi J.W., Chun H.J., Choi K.S., "Synthesis of chitosan derivatives with quaternary ammonium salt and their antibacterial activity", Polym. Bull., 1997, 38, 387.
Kotze A.F., Lueβen H.L., Leeuw B.J., Boer B.G., Verhoef J.C., Junginger H.E., "N-trimethyl chitosan chloride as a potential absorption enhancer across mucosal surfaces: In vitro evaluation in intestinal epithelial cells (Caco-2)", Pharmaceutical Research, 1997, 14, 1197.
Kotze A.F., Thanou M., Lueben H.L., de Boer A.G., Verhoef J.C., Junginger H.E, "Effect of the degree of quaternization of N-trimethyl chitosan chloride on the permeability of intestinal epithelial cells (Caco-2)" Eur. J. Pharm. Biopharm., 1999, 47, 269.

(56) References Cited

OTHER PUBLICATIONS

Le Berre A., Delacroix A., "L'addition des sels d'amines tertiaires aux composés éthyléniques électrophiles. II.—Cinétique de l'addition des sels de pyridinium à l'acrylamide en solution aqueuse", Bull. Soc. Chim. France, 1973, 640, 647. [With English abstract].

Lee J.K. Kim S.U., Kim J.H., "Modification of chitosan to improve its hypocholesterolemic capacity", Biosci. Biotechnol. Biochem., 1999, 63, 833.

Lee J.K., Kim S.Y., Kim S.U., Kim J.H., "Synthesis of cationic polysaccharide derivatives and their hypocholesterolaemic capacity", Biotechnol. Appl. Biochem., 2002, 35, 181.

Lemieux C, et al. 2005. "Hypolipidemic action of the SERM acolbifene is associated with decreased liver MTP and increased SR-BI and LDL receptors", J Lipid Res 46: 1285-94.

Lim, S.H. et al. "Review of chitosan and its derivatives as antimicrobial agents and their uses as textile chemicals", J. Macromol. Sci.-Polym. Rev., 2003, C43, 223.

Luria MH. 1988. "Effect of low-dose niacin on high-density lipoprotein cholesterol and total cholesterol/high-density lipoprotein cholesterol ratio", Arch Intern Med 148: 2493-5.

Muzzarelli R.A.A., Tanfani F., "The N-permethylation of chitosan and the preparation of N-trimethyl chitosan iodide", Carbohydr. Polym., 1985, 5, 297.

Nicolosi RJ, Wilson TA, Krause BR. 1998. "The ACAT inhibitor, CI-1011 is effective in the prevention and regression of aortic fatty streak area in hamsters", Atherosclerosis 137: 77-85.

Peter M.J., "Chitin and Chitosan from animal sources", In Biopolymers, vol. 6: Polysaccharides II: Polysaccharides from Eukaryotes, Vandamme E.J., De Baets S., Steinbüchel A. [Eds], Wiley-VCH, York, 2002, p. 488.

Polnok A., et al., "Influence of methylation process on the degree of quaternization of N-trimethyl chitosan chloride", Eur. J. Pharm. Biopharm., 2004, 57, 77-83.

Runarsson O.V., et al., "Antibacterial activity of methylated chitosan and chitooligomer derivatives: Synthesis and structure activity relationships", Eur. Polym. J., 2007, 43, 2660-2671.

Sahni S., Chopra S., Ahmad F.J., Khar R.K., "Potential prospects of chitosan derivative trimethyl chitosan chloride (TMC) as a polymeric absorption enhancer: synthesis, characterization and applications", Journal of Pharmacy and Pharmacology, 2008, 60, 1111.

Sieval A.B., Thanou M., Kotze A.F., Verhoef J.C., Brussee J., Junginger H.E., "Preparation and NMR characterization of highly substituted N-trimethyl chitosan chloride", Carbohydr. Polym., 1998, 36, 157-165.

Snyman D., Hamman J.H., Kotze A.F., "Evaluation of the mucoadhesive properties of N-trimethyl chitosan chloride", Drug Dev. Ind. Pharm., 2003, 29, 61.

Snyman D., Hamman J.H., Kotze J.S., Rollings J.E., Kotze A.F., "The relationship between the absolute molecular weight and the degree of quaternisation of N-trimethyl chitosan chloride", Carbohydr Polym., 2002, 50, 145-150.

\* cited by examiner

N,N,N-TRIALKYLAMINOPOLYMERS, METHODS OF THEIR PREPARATION AND USES THEREOF

CROSS REFERENCE TO RELATED APPLICATIONS

This application is a National Entry Application of PCT application no PCT/CA2012/050399 filed on Jun. 13, 2012 and published in English under PCT Article 21(2), which itself claims benefit of U.S. provisional application Ser. No. 61/496,255, filed on Jun. 13, 2011. All documents above are incorporated herein in their entirety by reference.

FIELD OF THE INVENTION

The present invention relates generally to N,N,N-trialkylaminopolymers. More specifically, the invention relates to N,N,N-trialkylaminopolysaccharides. Also, the invention also relates to N,N,N-trialkylchitosan, methods of preparation thereof, and their various uses, for example in the pharmaceutical, neutraceutical and cosmeceutical fields.

BACKGROUND OF THE INVENTION

Chitin is a long-chain polysaccharide of β-(1-4)-linked N-acetyl-D-glucosamine units and is found in many places throughout the natural world. It is the main component of the cell walls of fungi, the exoskeletons of arthropods such as crustaceans (e.g., crabs, lobsters and shrimps (including *Pandalus Borealis*)) and insects, the radulas of mollusks, and the beaks of cephalopods, including squid and octopuses. It is the second most common natural polysaccharide with an annual world production estimated at $2.3 \times 10^9$ tons (see Biopolymers, Vol. 6: Polysaccharides II: Polysaccharides from Eukaryotes, Vandamme E. J., De Baets S., Steinbüchel A., Wiley-VCH, New York, 2002, p. 488.).

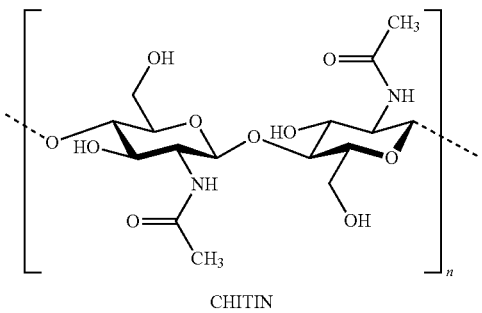

CHITIN

Chitosan, a poly[β-(1→4)-2-amino-2-deoxy-D-glucopyranose], is a biodegradable, biocompatible and non-toxic linear aminopolysaccharide obtained by deacetylating chitin. Full deacetylation of chitin produces chitosan with a degree of deacetylation (DD) of 100% and comprised only of 3-(1-4)-linked D-glucosamine (deacetylated units):

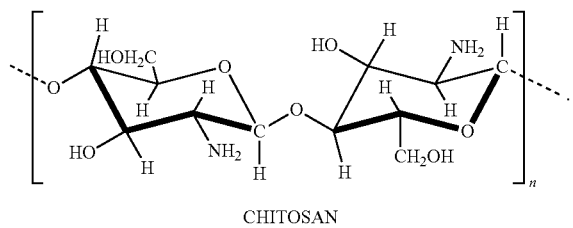

CHITOSAN

Chitosan with degrees of deacetylation (DD) smaller than 100% further comprises some original N-acetyl-D-glucosamine units. The degree of deacetylation of commercially available chitosan is usually in the range of 50-100%.

Chitosan is one of a few biopolymers that is cationic when protonated. Cationic polymers can generally adsorb on the cell walls of bacteria and thus act as antibacterials. For example, many studies outline the efficacy of chitosan in wound treatment. Utilization of chitosan in other applications has however been limited due to its insolubility in water when in neutral form. Its solubility is limited to diluted aqueous acid solution of pH<6.5.

N,N,N-trimethylchitosan (TMC) is a polycation generally obtained by methylating chitosan. It has the following ideal chemical formula:

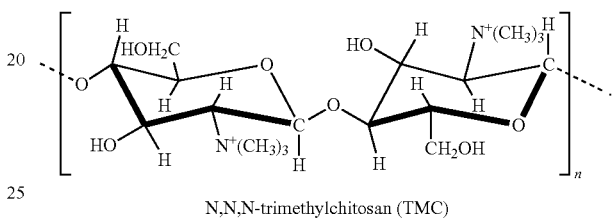

N,N,N-trimethylchitosan (TMC)

with a counterion to balance the electrical charge.

However, such an "ideal" TMC has never been produced. In fact, TMC reported in the literature has low degrees of quaternization (DQ) of the nitrogen atom (30-40% at most), which means that at least some D-glucosamine units only bear zero, one or two methyl groups on their nitrogen atom, rather than bearing three of them.

Typically, methods of producing TMC comprise carrying out successive methylation reactions on chitosan, using iodomethane (methyl iodide) or dimethylsulfate in the presence of a base, often sodium hydroxide, under various experimental conditions (see Curti E., Britto D., Campana-Filho S. P., *Macromol. Biosci.*, 2003, 3, 571-576 and Hamman J. H., Kotzé A. F., *Drug Dev. Ind. Pharm.*, 2001, 27, 373-380). However, methylation of chitosan under these conditions leads to the formation of a mixture of unmethylated, mono, di and trimethylated amines.

Indeed, chemical modification of polysaccharides presents many difficulties such as a lack of solubility of the polysaccharides in many organic and inorganic solvents (including water), the presence of various other chemical functions (thus the modification must be regioselective) and the high number of repeating units. Nevertheless, the synthesis of TMC has been the subject of many scholarly papers as it provides a polycationic chitosan derivative that is soluble in water. The formation of TMC indeed introduces positive charges and thus provides a water-soluble product in a wide pH range even when partially quaternized. It is thus desirable to produce TMC having a high degree of quaternization.

It has further been reported that attempts to increase the degree of quaternization to higher than 30-40% result in methylation of the oxygen atoms of the OH groups at position 3 and/or position 6 to an extent, which is referred to as the degree of O-substitution (O-DS). High degrees of O-substitution lead to a decrease in the TMC solubility in water as hydrophilic —OH groups are replaced by more hydrophobic —$OCH_3$ groups. It is thus desirable to produce TMC having a low degree of O-substitution.

Chitosan having high degrees of quaternization (DQ) on chitosan has been obtained (DQ of 90.5%) in a process involving three methylation steps, using iodomethane and sodium hydroxide; however, these conditions also lead to high degrees of O-substitution, particularly at positions 3 and 6 (O-3 and O-6 methylation), respectively of 82.8 and 98.5% (Polnok A., et al., *Eur. J. Pharm. Biopharm.*, 2004, 57, 77-83). The formation of methyl ether (O-methylation) by substitution of alcohol groups undesirably leads to a decreasing solubility of chitosan derivatives and possibly to a water insoluble product (Curti E., Britto D., Campana-Filho S. P., *Macromol. Biosci.*, 2003, 3, 571-576, Polnok A., et al., *Eur. J. Pharm. Biopharm.*, 2004, 57, 77-83, and Snyman D., Hamman J. H., Kotze J. S., Rollings J. E., Kotzé A. F., *Carbohydr. Polym.*, 2002, 50, 145-150).

Moreover, the use of sodium hydroxide or a strong alkaline environment decreases the molecular weight of the polymer. With experimental conditions that prevent O-methylation, low degrees of quaternization have generally been obtained (Polnok A., et al., Eur. J. Pharm. Biopharm., 2004, 57, 77-83).

Alternatively, when N,N-dimethylaminopyridine was used as a base instead of sodium hydroxide to avoid degradation of chitosan, low DQs (7.3-9.6%) were obtained (Hamman J. H., Kotzé A. F., *Drug Dev. Ind. Pharm.*, 2001, 27, 373-380).

TMC has also been synthesized using dimethylsulfate as the methylating agent (Britto D., Forato L. A., Assis O. B. G., *Carbohydr. Polym.*, 2008, 74, 86-91, Britto D., Assis B. G. O., *Carbohydr. Polym.*, 2007, 69, 305, and Britto D., Assis B. G. O., *Intl. J. Biol. Macromol.*, 2007, 41, 198).

Chitosan has also been N-permethylated by reaction with formaldehyde followed with sodium borohydride. The N-permethylated chitosan was reacted with iodomethane to obtain TMC. The resulting TMC iodide has a high degree of O-substitution of 60% and exhibits antibiotic activity, but is insoluble in water (Muzzarelli R. A. A., Tanfani F., *Carbohydr. Polym.*, 1985, 5, 297).

Preparation of mixed N,N,N-trialkylchitosan derivatives has also been reported with different alkyl iodide (Avadi M. R., Zohuriaan-Mehr M. J., Younessi P., Amini M., Rafiee Tehrani M., Shafiee A., *J. Bioact. Compat. Polym.*, 2003, 18, 469 and Bayat A., Sadeghi A. M. M., Avadi M. R., Amini M., Rafiee-Tehrani M., Shafiee A., Majlesi R., Junginger H. E., *J. Bioact. Compat. Polym.*, 2006, 21, 433).

TMC has drawn interest because of its multiple uses. Known uses of TMC include for example:

increasing the absorption of molecules through mucosae (for example through the intestine wall), controlled release of various substances including genes and proteins, and use as an antimicrobial agent.

N,N,N-trimethylchitosan has an increased density of positive charge (compared to chitosan) and it has been shown to open the tight junctions of epithelial cells. It has thus been proven to be a potent intestinal absorption enhancer for hydrophilic and macromolecular drugs in physiological pH (Thanou M., Florea B. I., Langemeyer M. W. E., Verhoef J. C., Junginger H. E., *Pharm. Res.*, 2000, 17, 27; Thanou M., Verhoef J. C., Verheijden J. H. M., Junginger H. E., *Pharm. Res.*, 2001, 18, 823; Thanou M., Kotzé A. F., Scharringhausen T., Leuben H. L., De Boer A. G., Verhoef J. C., Junginger H. E., *J. Controlled Release*, 2000, 64, 15; Thanou M., Verhoef J. C., Junginger H. E., *Adv. Drug Delivery Rev.*, 2001, 52, 117; and Florea B. I., Thanou M., Junginger H. E., Borchard G., *J. Control. Release*, 2006, 110, 353). The density of positive charge is known to have an important effect on drug absorption enhancing properties (Kotzé A. F., LueEn H. L., Leeuw B. J., Boer B. G., Verhoef J. C., Junginger H. E., *Pharmaceutical Research*, 1997, 14, 1197; and Kotzé A. F., Thanou M., Lueben H. L., de Boer A. G., Verhoef J. C., Junginger H. E., *Eur. J. Pharm. Biopharm.*, 1999, 47, 269). It has been reported that the higher the degree of quaternization, the greater the increase in absorption.

According to *J. Pharm. Sci.*, 2008, 97(5), 1652-1680, polymers increasing transepithelial penetration are polycations (chitosan, poly-L-arginine (poly-L-Arg), aminated gelatin), polyanions (N-carboxymethylchitosan, poly (acrylic acid)) and thiolated polymers (carboxymethyl cysteine-cellulose, polycarbophil (PCP)-cysteine, chitosan-thiobutylamidine, chitosan-thioglycolic acid, chitosan-glutathione conjugate).

TMC has been used in certain other applications such as in gene delivery, in colonic drug delivery and as an antibacterial (Rünarsson Ö. V., et al., *Eur. Polym. J.*, 2007, 43, 2660-2671; Borchard G., *Adv. Drug Delivery Rev.*, 2001, 52, 145; Dodou D., Breedveld P., Wiering a P. A., *Euro. J. Pharm. Biopharm.*, 2005, 60, 1; Kim C. H., Choi J. W., Chun H. J., Choi K. S., *Polym. Bull.*, 1997, 38, 387; Kean T., Roth S., Thanou M., *J. Control. Release*, 2005, 103, 643; and Jia Z., Shen D., Xu W., *Carbohydr. Res.*, 2001, 333, 1). A structure-activity relationship study reveals that N-quaternization on chitosan and on chitooligomers was responsible of the antibacterial activity against *Staphylococcus aureus* at pH 7.2 (Rünarsson Ö. V., et al., *Eur. Polym. J.*, 2007, 43, 2660-2671).

Cationic polymers, including protonated chitosan, are known to possess antibacterial properties (Lim, S. H. et al. *J. Macromol. Sci.-Polym. Rev.*, 2003, C43, 223.). Factors affecting antibacterial activity of polymers generally are the structure, the molecular weight, the nature of the counterions, and the hydrophobicity (Kenawy, E. et al. *Biomacromolecules*, 2007, 8, 1359-1384). The killing time can be as low as 30 min. for chitosan (El-Sharif, A. A. et al. *Curr. Microbiol.*, 2011, 62, 739-745).

Additionally, hydrophilic biopolymers generally are known to have an emollient effect.

Accordingly, there thus remains a need for improved methods of producing N,N,N-trialkylaminopolymers, particularly N,N,N-trialkylaminopolysaccharides that have high degrees of quaternization and low degrees of other heteroatom-substitution. Particularly, there is a need for improved methods of producing N,N,N-trialkylchitosan having a high degree of quaternization and a low degree of O-substitution.

SUMMARY OF THE INVENTION

The present inventor has designed a novel and improved method of preparing an N,N,N-trialkylchitosan. The method leads to N,N,N-trialkylchitosan having a high degree of quaternization and a low degree of O-substitution. N,N,N-trialkylchitosan produced by the method according to the invention has various uses. The method according to the invention can be applied in the preparation of N,N,N-trialkylaminopolymers that have other heteroatoms different from N. More specifically, the method according to the invention can be applied to N,N,N-trialkylaminopolysaccharides.

In an embodiment, the method involves a first step of alkylating an amino polymer to produce an N,N-dialkylaminopolymer having a high degree of N-substitution, with no formation of the N,N,N-trialkylaminopolymer. The method also involves a subsequent step of alkylating the N,N-dialkylaminopolymer to produce the N,N,N-trialkylaminopolymer. More specifically when the N,N-dialkylaminopolymer is obtained by a reductive amination reaction involving the use of an aldehyde and formic acid (Escheweiler-Clarke reaction). The alkylation reaction of the N,N-dialkylaminopolymer in the subsequent step involves the use of an alkylating agent and a base.

In an embodiment of the method according to the invention for the production of N,N,N-trimethylchitosan, chitosan having a degree of N-substitution (N-DS) of 2.0 is used.

The present invention thus provides:

1. A method of preparing an N,N,N-trialkylaminopolymer, comprising:
   a) providing an aminopolymer having one or more unsubstituted heteroatoms different from nitrogen atom;
   b) alkylating the aminopolymer to produce an N,N-dialkylaminopolymer, wherein substantially no N,N,N-trialkylaminopolymer is produced; and
   c) alkylating the N,N-diaminopolymer to produce the N,N,N-trialkylaminopolymer, wherein only a low percentage of the unsubstituted heteroatoms is alkylated.

2. A method of preparing an N,N,N-trialkylaminopolysaccharide, comprising:
   a) providing an aminopolysaccharide having one or more unsubstituted heteroatoms different from nitrogen atom;
   b) alkylating the aminopolysaccharide to produce an N,N-dialkylaminopolysaccharide, wherein substantially no N,N,N-trialkylaminopolysaccharide is produced; and
   c) alkylating the N,N-diaminopolysaccharide to produce the N,N,N-trialkylaminopolysaccharide,
wherein only a low percentage of the unsubstituted heteroatoms is alkylated.

3. A method according to item 1 or 2, wherein each alkyl group is independently, a $C_1$ to $C_6$ alkyl group, preferably a $C_1$ to $C_3$ alkyl group, which is saturated or unsaturated, branched or unbranched, optionally having a heteroatom, more preferably the alkyl group is independently the methyl group or the propyl group.

4. A method according to any one of items 1 to 3, wherein each unsubstituted heteroatom is independently oxygen or sulfur atom.

5. A method according to any one of items 1 to 4, wherein step b) is performed using an aldehyde and formic acid.

6. A method according to any one of items 1 to 4, wherein step b) is a reductive amination reaction.

7. A method according to item 5, wherein the aldehyde is a $C_1$ to $C_6$ aldehyde, preferably a $C_1$ to $C_3$ aldehyde, which is saturated or unsaturated, branched or unbranched, optionally having a heteroatom, more preferably the aldehyde is formaldehyde or propanal.

8. A method according to any one of items 1 to 7, wherein step c) is performed using an alkylating agent such as an alkyl halide or a dialkyl carbonate and a base, in a reaction solvent comprising an organic solvent, water and/or an alcohol.

9. A method according to item 1, further comprising a step of adding HCl, HBr or HI to produce the N,N,N-trialkylaminopolymer with a chloride, bromide or iodide counterion.

10. A method according to item 2, further comprising a step of adding HCl, HBr or HI to produce the N,N,N-trialkylaminopolysaccharide with a chloride, bromide or iodide counterion.

11. A method of preparing an N,N,N-trialkylchitosan, comprising:
   a) providing chitosan;
   b) alkylating chitosan to produce an N,N-dialkylchitosan, wherein substantially no N,N,N-trialkylchitosan is produced; and
   c) alkylating the N,N-dialkylchitosan to produce the N,N,N-trialkylchitosan, wherein only a low percentage of the unsubstituted oxygen atoms is alkylated.

12. A method according to item 11, wherein each alkyl group is independently, a $C_1$ to $C_6$ alkyl group, preferably a $C_1$ to $C_3$ alkyl group, which is saturated or unsaturated, branched or unbranched, optionally having a heteroatom, more preferably the alkyl group is independently the methyl group or the propyl group.

13. A method according to item 11 or 12, wherein the N,N-dialkylchitosan has a degree of N-substitution (N-DS) of about 2.0.

14. A method according to claim any one of items 11 to 13, wherein chitosan has a degree of deacetylation (DD) of about 100%, about 95% or more, about 90% or more, about 85% or more, about 80% or more, about 75% or more, about 70% or more, about 65% or more, or about 60% or more.

15. A method according to any one of items 11 to 14, wherein step b) is performed using an aldehyde and formic acid.

16. A method according to item 15, wherein the aldehyde is a $C_1$ to $C_6$ aldehyde, preferably a $C_1$ to $C_3$ aldehyde, which is saturated or unsaturated, branched or unbranched, optionally having a heteroatom, more preferably the aldehyde is formaldehyde or propanal.

17. A method according any one of items 11 to 14, wherein step b) is a reductive amination reaction.

18. A method according to any one of items 11 to 17, wherein step c) is performed using an alkylating agent and a base, in a reaction solvent.

19. A method according to item 18, wherein the alkyl group in the alkylating agent is a $C_1$ to $C_6$ alkyl group, preferably a $C_1$ to $C_3$ alkyl group, which is saturated or unsaturated, branched or unbranched, optionally having a heteroatom, more preferably the alkyl group in the alkylating agent is the methyl group or the propyl group 20. A method according to item 18 or 19, wherein the alkylating agent is a haloalkane or a dialkylcarbonate, preferably the alkylating agent is iodomethane, iodopropane or dimethylcarbonate.

21. A method according to any one of items 18 to 20, wherein the base is a hydroxide salt or an alkali carbonate or bicarbonate.

22. A method according to any one of items 18 to 21, wherein the base is sodium hydroxide or sodium carbonate.

23. A method according to item 18, wherein the reaction solvent is N,N-dimethyl-formamide (DMF), water, an alcohol, a mixture of DMF and water, a mixture of DMF and an alcohol or a mixture of alcohols.

24. A method according to any one of items 11 to 23, wherein at least one of step b) and step c) is performed using a microwave.

25. A method according to any one of items 11 to 24, further comprising a step of adding HCl, HBr or HI to produce the N,N,N-trialkylchitosan with a chloride, a bromide or an iodide counterion.

26. N,N,N-trimethylchitosan produced according to the method of any one of items 1 to 25.

27. N,N,N-trimethylchitosan produced according to the method of any one of items 1 to 25, in association with a carbonate, halide, bromide, iodide or hydroxide counterion.

28. N,N,N-trimethylchitosan produced according to the method of any one of items 1 to 25 having a degree of quaternization of about 30% or more and a degree of O-substitution of about 95% or less.

29. N,N,N-trimethylchitosan having a degree of quaternization of about 30% or more and a degree of O-substitution of about 95% or less.

30. N,N,N-trimethylchitosan produced according to the method of any one of items 1 to 25, having a degree of quaternization of about 35% or more, about 40% or more, about 45% or more, about 46% or more, about 50% or more, about 55% or more, about 60% or more, about 65% or more, about 70% or more, about 75% or more, about 80% or more, about 85% or more, about 90% or more, about 95% or more, about 98% or more, or about 100%.

31. N,N,N-trimethylchitosan having a degree of quaternization of about 35% or more, about 40% or more, about 45% or more, about 46% or more, about 50% or more, about 55% or more, about 60% or more, about 65% or more, about 70% or more, about 75% or more, about 80% or more, about 85% or more, about 90% or more, about 95% or more, about 98% or more, or about 100%.

32. N,N,N-trimethylchitosan produced according to the method of any one of items 1 to 25, having a degree of O-substitution of about 90% or less, about 85% or less, about 80% or less, about 75% or less, about 70% or less, about 65% or less, about 60% or less, about 45% or less, about 40% or less, about 35% or less, about 30% or less, about 25% or less, about 20% or less, about 15% or less, about 10% or less, about 5% or less, about 2% or less, or about 0%.

33. N,N,N-trimethylchitosan having a degree of O-substitution of about 90% or less, about 85% or less, about 80% or less, about 75% or less, about 70% or less, about 65% or less, about 60% or less, about 45% or less, about 40% or less, about 35% or less, about 30% or less, about 25% or less, about 20% or less, about 15% or less, about 10% or less, about 5% or less, about 2% or less, or about 0%.

34. N,N,N-trimethylchitosan produced according to the method of any one of items 1 to 25, having a degree of deacetylation of about 100%, about 95% or more, about 90% or more, about 85% or more, about 80% or more, about 75% or more, about 70% or more, about 65% or more, or about 60% or more.

35. N,N,N-trimethylchitosan having a degree of deacetylation of about 100%, about 95% or more, about 90% or more, about 85% or more, about 80% or more, about 75% or more, about 70% or more, about 65% or more, or about 60% or more.

36. A pharmaceutical composition comprising N,N,N-trimethylchitosan according to any one of items 26 to 35 and a pharmaceutically acceptable carrier.

37. A method of treating hypercholesterolemia, comprising administering N,N,N-trimethylchitosan according to any one of items 26 to 35 or the pharmaceutical composition according to item 36 to a subject in need thereof.

38. A method of promoting healing of a wound, the method comprising applying locally to the wound a skin care product comprising N,N,N-trimethylchitosan according to any one of items 26 to 35.

39. A method of increasing absorption of a molecule through mucosae, comprising administering to a subject the molecule together with N,N,N-trimethylchitosan according to any one of items 26 to 35 or the pharmaceutical composition according to item 36.

40. A method of performing controlled release of a molecule, comprising administering to a subject the molecule together with N,N,N-trimethylchitosan according to any one of items 26 to 35 or the pharmaceutical composition according to item 36.

41. Use of N,N,N-trimethylchitosan according any one of items 26 to 35 or the pharmaceutical composition according to item 36, for treating hypercholesterolemia in a subject.

42. Use of N,N,N-trimethylchitosan according to any one of items 26 to 35 or the pharmaceutical composition according to item 35, for promoting healing of a wound in a subject.

43. Use of N,N,N-trimethylchitosan according to any one of items 26 to 35 or the pharmaceutical composition according to item 36, for increasing absorption of a molecule through mucosae.

44. Use of N,N,N-trimethylchitosan according to any one of items 26 to 35 or the pharmaceutical composition according to item 36, for the controlled release of a molecule.

45. Use of N,N,N-trimethylchitosan according any one of items 26 to 35 or the pharmaceutical composition according to item 36 in combination with a hypocholesterolemic agent which is a HMG-CoA reductase inhibitor or a cholesterol absorption inhibitor.

46. Use of the N,N,N-trimethylchitosan according to any one of items 26 to 35 as a hypocholesterolemic agent.

47. Use of the N,N,N-trimethylchitosan according to any one of items 26 to 35 as a polyquaternium.

48. Use of the N,N,N-trimethylchitosan according any one of items 26 to 35 as an emollient.

49. Use of the N,N,N-trimethylchitosan according any one of items 26 to 35 as an antimicrobial agent.

50. N,N,N-trimethylchitosan according to any one of items 26 to 35 or the pharmaceutical composition of item 36 for the treatment of hypercholesterolemia.

51. N,N,N-trimethylchitosan according to any one of items 26 to 35 or the pharmaceutical composition of item 36, for the promotion of wound healing.

52. N,N,N-trimethylchitosan according to any one of items 26 to 35 or the pharmaceutical composition according to item 36, for administration in combination with a hypocholesterolemic agent which is a HMG-CoA reductase inhibitor or a cholesterol absorption inhibitor.

53. A natural health product comprising N,N,N-trimethylchitosan of any one of items 26 to 35.

54. A neutraceutical product comprising N,N,N-trimethylchitosan of any one of items 26 to 35.

55. A personal care product comprising N,N,N-trimethylchitosan of any one of items 26 to 35.

56. A personal care product of item 55, wherein the personal care product is a hair care product or a skin care product.

57. The personal care product of item 55 or 56, for the promotion of wound healing.

58. An ophtalmic product comprising N,N,N-trimethylchitosan of any one of items 26 to 35.

59. A cosmeceutical product comprising N,N,N-trimethylchitosan of any one of items 26 to 35.

60. The cosmeceutical product of item 59, for the promotion of wound healing.

61. A cosmetic product comprising N,N,N-trimethylchitosan of any one of items 26 to 35.

62. Use of N,N,N-trimethylchitosan according any one of items 26 to 35, in the preparation of a medicament for treating hypercholesterolemia in a subject.

63. Use of N,N,N-trimethylchitosan according to any one of items 26 to 35, in the preparation of a medicament for promoting healing of a wound in a subject.

64. Use of N,N,N-trimethylchitosan according to any one of items 26 to 35, in the preparation of a medicament for increasing absorption of a molecule through mucosae.

65. Use of N,N,N-trimethylchitosan according to any one of items 26 to 35, in the preparation of a medicament for the controlled release of a molecule.

66. N,N,N-trialkylaminopolymer produced according to the method of item 1.

67. N,N,N-trialkylaminopolysaccharide produced according to the method of item 2.

68. N,N,N-tripropylchitosan produced according to the method of any one of items 1 to 25.

DETAILED DESCRIPTION OF THE INVENTION

Figure 1:
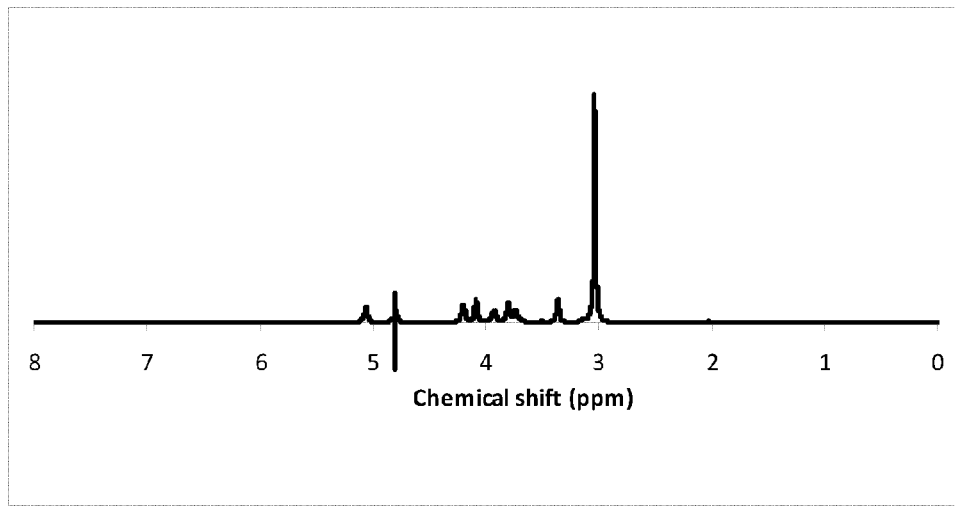
FIG. 1 is the NMR spectrum of DMC.HCl in $D_2O$.

The present invention provides, according to an aspect, a method of preparing N,N,N-trialkylaminopolymers that have other unsubstituted heteroatoms different from N, particularly N,N,N-trialkylpolysaccharides. In embodiments, the alkyl groups are each independently a $C_1$ to $C_6$, preferably $C_1$ to $C_3$ alkyl group, which is saturated or unsaturated, branched or unbranched. More preferably, the alkyl group is the methyl group or the ethyl group. The other heteroatoms present can be O or S. Only a low percentage of the other heteroatoms is alkylated during the preparation method according to the invention.

In embodiments of the invention, the N,N-dialkylaminopolymer and the N,N-dialkylaminopolysaccharide are the N,N-dimethylaminopolymer and the N,N-dimethylaminopolymer, respectively. In these embodiments, preparation of the N,N-dialkylaminopolymer and N,N-dialkylaminopolymer is performed by reductive amination involving use of an aldehyde such as formaldehyde or propanal and formic acid (Eschweiler-Clarke reaction). In embodiments of the invention where the alkyl group is not methyl, a skilled person will understand that a suitable alkylating reaction is performed, which stops at the double N-alkylation.

The N,N-dimethylaminopolymer and N,N-dimethylaminopolysaccharide are subsequently subjected to an alkylation reaction involving use of an alkylating agent and a base. The alkylation reaction is performed in a suitable solvent which may or may not include an organic solvent. A suitable reaction solvent can be dimethyl formamide (DMF), water, and/or an alcohol. The alkylating agent can be an alkyl halide or a dialkyl carbonate.

The invention further provides, according to another aspect, a method for the preparation of N,N,N-trimethylchitosan (TMC). Preparation of N,N-dimethylchitosan is performed by reductive amination involving use of formaldehyde and formic acid (Eschweiler-Clarke reaction). N,N-dimethylchitosan is subsequently subjected to an alkylation reaction involving use of an alkylating agent and a base. The alkylation reaction is performed in a reaction solvent which is DMF, water, an alcohol, a mixture of DMF and water, a mixture of DMF and an alcohol or a mixture of alcohol. A suitable base used in the alkylation reaction is sodium hydroxide or sodium carbonate. In embodiments of the invention, the alkylation reaction is performed in a microwave. Chitosan used in the method according to the invention has a degree of N-substitution (N-DS) of about 2.0. Only a low percentage the O atoms that are unsubstituted are methylated during the preparation method.

In an aspect, the present invention provides N,N,N-trimethylchitosan (TMC) with a degree of quaternization of about 30% or more and a degree of O-substitution (O-DS) of about 95% or less.

Herein, the degree of quaternization (DQ) of the N,N,N-trimethylchitosan (TMC) is the ratio of the number of nitrogen atoms of the TMC bearing three methyl groups to the total number of nitrogen atoms of the TMC. The degree of quaternization can be expressed as a ratio or as a percentage.

In embodiments, the TMC has a degree of quaternization of about 35% or more, about 40% or more, about 45% or more, about 46% or more, about 50% or more, about 55% or more, about 60% or more, about 65% or more, about 70% or more, about 75% or more, about 80% or more, about 85% or more, about 90% or more, about 95% or more, about 98% or more, or about 100%.

Herein, the degree of O-substitution (O-DS) is the ratio of the number of oxygen atoms at the 3 and 6 positions of the TMC bearing a methyl group to the total number of oxygen atoms at the 3 and 6 positions of the TMC. The degree of O-substitution (O-DS) can be expressed as a ratio or as a percentage. The degree of O-substitution is low. Also, in the N,N,N-trialkylaminopolymers and N,N,N-trialkylaminopolysaccharides according to the invention wherein the other heteroatoms different from nitrogen atom are not oxygen atoms, the degree of substitution of such heteroatom is low. As used herein, a "low degree of substitution" of the heteroatoms different from nitrogen atom such as oxygen atom means a degree of substitution of about 90% or less, 85% or less about 85% or less, about 80% or less, about 75% or less, about 70% or less, about 65% or less, about 60% or less, about 45% or less, about 40% or less, about 35% or less, about 30% or less, about 25% or less, about 20% or less, about 15% or less, about 10% or less, about 5% or less, about 2% or less, or about 0%.

In embodiments, the TMC has a degree of O-substitution of about 90% or less, 85% or less about 85% or less, about 80% or less, about 75% or less, about 70% or less, about 65% or less, about 60% or less, about 45% or less, about 40% or less, about 35% or less, about 30% or less, about 25% or less, about 20% or less, about 15% or less, about 10% or less, about 5% or less, about 2% or less, or about 0%.

The N,N,N-trimethylchitosan of the invention is a polycation and is therefore in association, at least in solid form, with a counterion. Any suitable counterion can be used. The skilled person will select this counterion depending on the end use of the TMC. In embodiments, the counterion is a carbonate ion ($CO_3^{2-}$), a halide ion, such as a chloride ion (Cl—) or iodide (I—), or a hydroxide ion (OH—).

The N,N,N-trimethylchitosan of the invention also has a degree of deacetylation (DD) that depends on the DD of the chitosan from which the N,N,N-trimethylchitosan is made. Herein, the degree of deacetylation of the TMC or chitosan is the ratio of the number of nitrogen atoms of the TMC or chitosan not bearing an acetyl group to the total number of nitrogen atoms of the TMC or chitosan. The degree of deacetylation can be expressed as a ratio or as a percentage.

It is to be noted that only the nitrogen atoms of the chitosan not bearing an acetyl group can bear three methyl groups. Therefore, the highest DQ obtainable for a given TMC directly depends on the DD of the chitosan used for its manufacture. For example, a chitosan with a DD of 85% only has 85% of its nitrogen atoms available to be quaternized. Therefore, the highest DQ for TMC produced from this chitosan will be 85%.

In embodiments, the TMC (and also the chitosan from which it has been prepared) has a DD of about 100%, about 95% or more, about 90% or more, about 85% or more, about 80% or more, about 75% or more, about 70% or more, about 65% or more, or about 60% or more.

As will be apparent to the skilled person, the TMC of the invention, being a derivative of chitosan, which is biodegradable, is expected to be biodegradable.

Depending on the counterion, the TMC of the invention can be soluble or insoluble in water. For example, the inventor has observed that TMC carbonate is insoluble in water, while TMC chloride is soluble in this solvent. This is different from the prior art where the insolubility is generally due to excessive O-methylation or to the presence of sulfate anions.

Synthesis

There is provided a method of preparing TMC. The inventor first tried to produce TMC directly from chitosan (with a DD of 95-96%) using an alkylation agent and a base as taught in previous reports, but only TMCs with low DQs were obtained. For example, in a water:DMF mixture, the DQ can be around 29% with 59% dimethylated units, and 2% monomethylated units. Further attempts using various new alkylating agents and bases were similarly unsuccessful. For example, methylation using dimethylsulfate leads to an insoluble product.

As per the studies described herein, the inventor has designed and developed an improved method of preparing TMC.

In the method according to the invention, N,N-dimethylchitosan (DMC) essentially has all nitrogen atoms substituted (degree of N-substitution of about 2.0).

Firstly, the method according to the invention involves the preparation of N,N-dimethylchitosan. This first fart of the method comprising:
providing chitosan; and
methylating the chitosan through an Eschweiler-Clarke reaction using formic acid and formaldehyde.

The method allows for the production of DMC with essentially all nitrogen atoms double methylated (i.e. a degree of N-substitution of about 2.0). The method also allows for the production of DMC in good yields and purities.

Advantageously, the chitosan used as a starting material, can have a DD of about 95-96% and a viscosity of 150 cps (1% aqueous acetic acid), which corresponds to a commercial grade chitosan that is available at low cost. Chitosan is available in various molecular weights, which allows obtaining DMC (and ultimately TMC) of correspondingly various molecular weights. In embodiments of the invention, the chitosan has a DD of about 100%, about 95% or more, about 90% or more, about 85% or more, about 80% or more, about 75% or more, about 70% or more, about 65% or more, or about 60% or more, about 55% or more, or about 50% or more.

Advantageously, the Eschweiler-Clarke reaction can be performed in water and with reduced quantities of reactants, notably formic acid. The Eschweiler-Clarke reaction or Eschweiler-Clarke methylation is a chemical reaction whereby a primary (or secondary) amine is methylated using excess formic acid and formaldehyde. This reductive amination reaction does not produce quaternary ammonium salts, but instead stops at the tertiary amine stage.

The mechanism of Eschweiler-Clark reaction is:

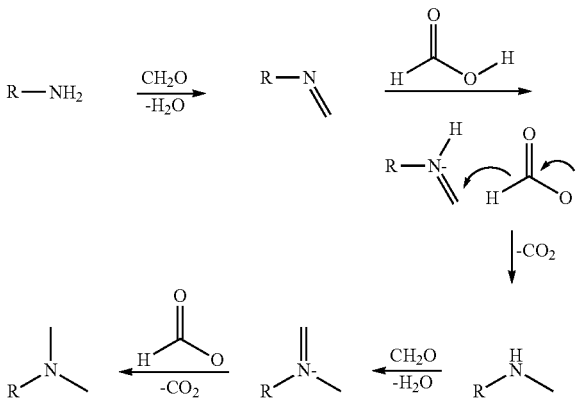

The first methylation of the amine begins with imine formation with formaldehyde. The formic acid acts as a source of hydride and reduces the imine to a secondary amine. The driving force is the formation of the gas carbon dioxide. Formation of the tertiary amine is similar. From this mechanism it is clear that a quaternary ammonium salt will never form, because it is impossible for a tertiary amine to form another imine or iminium ion.

Secondly, the method according to the invention involves the preparation of TMC. This second part of the method comprising:
providing N,N-dimethylchitosan having essentially all nitrogen atoms double methylated (i.e. a degree of N-substitution of about 2.0), and
methylating the N,N-dimethylchitosan using an alkylating agent and a base.

In embodiments, the alkylating agent is iodomethane.

In embodiments, the methylating step is carried out in an organic solvent, such as DMF.

In embodiments, the methylating step is carried out in a DMF:H$_2$O mixture, for example a 50:50 (v/v) mixture. In such a mixture, the water can be present in percentages of about 15% or more.

In other embodiments, the methylating step is carried out in water.

In other embodiments, the methylating step is carried out in water mixed with a water-miscible organic solvent. The purpose of this water-miscible organic solvent is to increase the miscibility of iodomethane in the reaction medium. Non-limiting examples of solvents include methanol and ethanol. They can be present in an amount of about 0% to about 50% and possibly more depending on the solubility of the exact reactants used in the reaction medium. In embodiments, the solvent is a water-methanol mixture, for example a 90:10 (v/v) mixture.

The avoidance of N,N-dimethylformamide (DMF), which is the usual solvent for methylating chitosan to produce TMC, eliminates the side-production of tetramethylammonium, which may occur when a stronger base such as sodium hydroxide is used. In cases where it is produced, the tetramethylammonium is to be eliminated during purification of TMC, for example by ultrafiltration.

In embodiments, the base is an alkali carbonate or bicarbonate, such as sodium bicarbonate or sodium carbonate. Using this base reduces the methylation of the alcohol groups at positions 3 and 6. Another advantage of using this base is that TMC carbonates are insoluble in water, which eases purification of TMC (which can then be effected by simple filtration) when water together with an organic solvent is used as the reaction solvent.

In other embodiments, the base is sodium hydroxide.

In an embodiment, the alkylating agent is iodomethane, the methylation step is carried out in water and the base is sodium bicarbonate. This embodiment is illustrated in the following scheme together with the production of DMC.

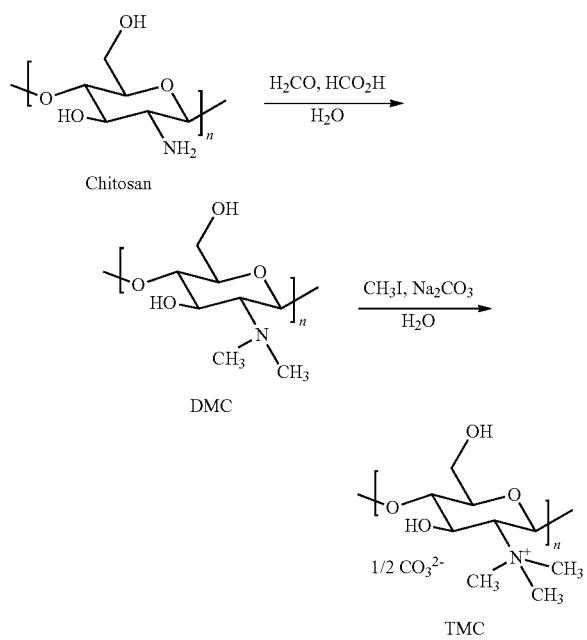

This avoids producing impurities and reduces or eliminates O-methylation. This also reduces costs and eliminates the need for ultrafiltration. The TMC carbonate thus produced can be transformed into TMC chloride by simple addition of HCl. It would also possibly be transformed into TMC chloride in the stomach, which contains HCl. Such TMC chloride is soluble in water, was obtained with excellent purity (see the examples below), high DQs and, finally, no O-alkylation was observed.

In embodiments, a salt such as NaI or NaCl, is additional used when methylating the N,N-dimethylchitosan using the alkylating agent and the base. In embodiments, this salt is NaI.

TMC has been successfully synthesized at the 10 g scale using the above method.

The above method of manufacturing TMC has several advantages:
  it provides a good control on the DQ (0% to 100%) through the variation of the reaction and the amount of reactants used,
  it provides a good control on the molecular weight and DD of the TMC (through selection of the chitosan used as a starting material as it is not significantly hydrolyzed during the reaction),
  TMC has low O-DS (methylation on the oxygen atoms at positions 3 and 6),
  TMC is provided in good yield and with good purity.

Also, compared to the prior art, the methylation step does not have to be repeated several times to obtain high DQs. When the reaction is performed in a microwave oven, an excess of iodomethane is used, but can be recycled and re-used.

In embodiments, the methods of the invention for manufacturing DMC and TMC use some Generally Recognized As Safe (GRAS) reactants and no organic solvents except for alcohols.

It will be apparent to a skilled person that the method according to the invention can be used for the quaternization of poly-L-arginine as well as other amino polymers.

Uses

TMCs in general and the compound of the invention in particular have several uses. They can be used to increase the absorption of molecules trough mucosae, which can be useful in the manufacture of vaccines and certain drugs. They can also be used for the controlled release of various substances including genes and proteins.

Hypocholesterolemic Agent

Hypercholesterolemia affects more than 4% of the general population (compared to 2% for diabetes) and in some countries 20-30% of people over 45-50 years. Hypercholesterolemia is the main risk factor for cardiovascular diseases, which are the leading cause of death in western societies (37% of all deaths in 1997).

The first line treatment for hypercholesterolemia is the administration of HMG-CoA reductase inhibitors (statins such as Lovastatin (Mevacor, Altoprev), Pravastatin (Pravachol), Simvastatin (Zocor), Fluvastatin (Lescol), Atorvastatin (Lipitor), Rosuvastatin (Crestor), Nivastatin, Mevastatin, Mevinolin, calcium Atorvastatin et Pitavastatin). However, it is estimated that 27-60% of patients on statin monotherapy do not reach their target level of low density lipoprotein cholesterol (LDL-C). Furthermore, statins have side effects such as myopathy.

Other methods are also used to reduce blood cholesterol levels. These include using cholesterol absorption inhibitors (Ezetimibe) and bile acid sequestrants (BAS) such as cholestyramine (Questran), colestipol (Colestid), sevelamer HCl (Renagel de Genzyme Corp.) and Covalesam (Welchol), which are synthetic resins. The BAS are positively charged and strongly interact with the negative charges on the bile salts. The BAS eliminate bile salts by sorption or precipitation, which causes their elimination in feces and thus prevents their absorption in the intestine. To maintain the required amount of bile salts, the liver will use cholesterol to produce bile acids, thereby reducing cholesterol levels.

There is also a natural BAS available over-the-counter: Cholestol™. It is a chitosan oligosaccharide of 40 kDa. Cholestol™ is water insoluble at all pHs.

TMCs in general and the compound of the invention in particular can also be used as hypocholesterolemic agents. Indeed, as shown in the Examples below, the TMC of the invention is a bile acid sequestrant. The electrostatic interactions between quaternized chitosan (positively charged) and bile salts (negatively charged) promotes the sequestration of the latter. Because of its high molecular weight, the compound of the invention is not absorbed by the body. Therefore, by binding to bile acids, the compound of the invention prevents their enterohepatic reabsorption and causes their elimination with the feces. This leads to an increased production of bile acids by the liver. The liver uses cholesterol to produce bile acids, which results in a decrease in plasma cholesterol levels.

The compound of the invention is thus useful for the treatment of hypercholesterolemia, especially light to moderate hypercholesterolemia. In the Examples below, tests have shown that the compound of the invention is a better bile acid sequestrant (sodium glycocholate and sodium taurocholate) than Cholestol™ and is about as efficacious as cholestyramine. It is believed that the solubility of the TMC of the invention make it more available for trapping bile acids in the intestines than insoluble products.

As such, the compound of the invention represents a natural alternative to the existing treatments. It could thus be part of a pharmaceutical composition, a natural health product, a neutraceutical product or a food product.

The compound of the invention can also be used as shown in the Examples below, for increasing the HDL/non-HDL cholesterol ratio.

Based on the results reported in the examples below, on the literature regarding prior art TMCs and on the fact that TMC is derived from chitosan, a natural non-toxic product, it is envisioned that TMC will exhibit no significant toxicity. In fact, the compound of the invention is hydrophilic and water soluble at intestinal pH, unlike cholestyramine and Cholestol™. It is thus envisioned that the hydrophilicity of TMC to decrease stomach pain, constipation, and/or diarrhea, which can be associated with the administration of cholestyramine and Cholestol™.

The compound of the invention can also be used in combination with the existing hypocholesterolemic agents, including, for example, HMG-CoA reductase inhibitors and/or cholesterol absorption inhibitors.

Polyquaternium and Emollient

"Polyquaternium" is the International Nomenclature for Cosmetic Ingredients (INCI) designation for several polycationic polymers that are used in the personal care industry. Polyquaternium is a neologism used to emphasize the presence of quaternary ammonium centers in the polymer. INCI has approved at least 37 different polymers under the polyquaternium designation. Different polymers are distinguished by the numerical value that follows the word "polyquaternium".

| Polyquaternium | Chemical Identity |
|---|---|
| Polyquaternium-1 | Ethanol, 2,2',2''-nitrilotris-, polymer with 1,4-dichloro-2-butene and N,N,N',N'-tetramethyl-2-butene-1,4-diamine |
| Polyquaternium-2 | Poly[bis(2-chloroethyl) ether-alt-1,3-bis[3-(dimethylamino)propyl]urea] |
| Polyquaternium-4 | Hydroxyethyl cellulose dimethyl diallylammonium chloride copolymer; Diallyldimethylammonium chloride-hydroxyethyl cellulose copolymer |
| Polyquaternium-5 | Copolymer of acrylamide and quaternized dimethylammoniumethyl methacrylate |
| Polyquaternium-6 | Poly(diallyldimethylammonium chloride) |
| Polyquaternium-7 | Copolymer of acrylamide and diallyldimethylammonium chloride |
| Polyquaternium-8 | |
| Polyquaternium-9 | |
| Polyquaternium-10 | Quaternized hydroxyethylcellulose |
| Polyquaternium-11 | Copolymer of vinylpyrrolidone and quaternized dimethylaminoethyl methacrylate |
| Polyquaternium-12 | |
| Polyquaternium-13 | |
| Polyquaternium-14 | |
| Polyquaternium-15 | Acrylamide-dimethylaminoethyl methacrylate methyl chloride copolymer |
| Polyquaternium-16 | Copolymer of vinylpyrrolidone and quaternized vinylimidazole |
| Polyquaternium-17 | |
| Polyquaternium-18 | |
| Polyquaternium-19 | |
| Polyquaternium-20 | |
| Polyquaternium-22 | Copolymer of Acrylic Acid and Diallyldimethylammonium Chloride |
| Polyquaternium-24 | |
| Polyquaternium-27 | |
| Polyquaternium-28 | Copolymer of vinylpyrrolidone and methacrylamidopropyl trimethylammonium |
| Polyquaternium-29 | |
| Polyquaternium-30 | |
| Polyquaternium-31 | |
| Polyquaternium-32 | Poly(acrylamide 2-methacryloxyethyltrimethyl ammonium chloride) |
| Polyquaternium-33 | |
| Polyquaternium-34 | |
| Polyquaternium-35 | |
| Polyquaternium-36 | |
| Polyquaternium-37 | Poly(2-methacryloxyethyltrimethylammonium chloride) |
| Polyquaternium-39 | Terpolymer of Acrylic Acid, Acrylamide and Diallyldimethylammonium Chloride |
| Polyquaternium-42 | |
| Polyquaternium-45 | |
| Polyquaternium-46 | Terpolymer of vinylcaprolactam, vinylpyrrolidone, and quaternized vinylimidazole |
| Polyquaternium-47 | Terpolymer of acrylic acid, methacrylamidopropyl trimethyl ammonium chloride, and methyl acrylate |

Polyquaterniums (PQs) are used in shampoos, conditioners, hair foams, hairsprays, hair dyes and hair gels, liquid soaps and lotions, creams for hands and body and contact lens solutions. Because they are positively charged, they neutralize the negative charges of most shampoos and hair proteins and help hair lie flat. Their positive charges also ionically bond them to hair and skin. Some have antimicrobial properties.

Commercially available PQs are generally positively charged water-soluble polymers with multiple quaternary amines that form ionic complexes with tensioactives (EP 1250118 B1). These physico-chemical properties (complexation and viscosity) are sought when formulating body care products. The data sheets of commercial PQs show several derivatives of the same molecule with varying molecular weights, degrees of quaternization and hydrophobicity (see for example the SoftCAT™ products by The Dow Chemical Company). This allows formulators to choose the specific derivative corresponding to their needs.

Current formulations of shampoos aim to do far more than simply cleaning hair. They often also aim at conditioning the hair, smoothing hair surface, easing hair do and having a creamy aspect. PQs play an important role in achieving these goals. Shampoos are now multifunctional (2 in 1 and 3 in 1) and incorporate a wide variety of ingredients (vitamins, silicones, protein derivatives . . . ).

Considering the large volumes of products involved as well as environmental and consumer health concerns, the cosmeceutical industry is turning to more natural and biodegradable products. The current PQs are however of synthetic origin or incorporate large synthetic parts.

PQs are used in cosmetics because they bind to negatively charged surfaces such as cell membranes and proteins. In addition, because of their polymeric nature, PQs (in proportions around 0.5%) increase the viscosity of the product, especially skin cream. A study of the toxicity of eleven PQs showed that the toxic dose ($EC_{50}$) is between <1.0 to 10 mg/L for ten of them, except polyquaternium-10 with low charge densities (Cumming J. L., Hawker D. W., Nugent K. W., Chapman H. F., *Journal of Environmental Science and Health* Part A, 2008, 43, 113).

Cationic polymers, such as PQs, form complexes (coacervation) with surfactants and thus act as a conditioner for the deposition of this complex on the hair and as a structuring agent for aqueous cosmetic compositions for hair or skin. When the molar ratio of ionic surfactant is equal to the molar ratio of positive charge of the polyquaternium (PQ), the viscosity of the solution is significantly reduced and a second phase forms (Gruber J. V., *Journal of Cosmetic Science,* 2009, 60, 385). The viscosity and turbidity of the solution of PQ is influenced by the structure and the molar ratio of surfactant.

Polyquaternium-10 is composed of a main chain of cellulose to which polyethylene glycol bearing a quaternary amine, has been grafted. It is used as an antibacterial agent in solutions for contact lenses.

TMCs in general, and the compound of the TMC invention in particular, can be used as a polyquaternium (PQ) and/or an emollient in personal care products, especially hair and skin products, such as shampoos, conditioners, hair foams, hairsprays, hair dyes, hair gels, liquid soaps and lotions, hand and/or body creams and the like.

The compound of the invention has a structure with quaternary amines that is similar to that of commercial PQs. Like them, it forms ionic complexes with natural and synthetic surfactants (e.g. bile salts and sodium dodecylsulfate) and therefore has similar properties. Moreover, the degree of quaternization (DQ) and the molecular weight of the compound of the invention can be controlled as with the commercial PQs and therefore allow optimizing its properties depending on the desired characteristics of the end product. Thus, the compound of the invention can replace commercial PQs.

The compound of the invention (a) is a derivative of chitosan, which is known to be non-toxic, and (b) does not show any toxicity during the in vivo tests described herein. It is therefore envisioned that the compounds of the invention will be acceptable in formulations that come into contact with the skin and/or scalp.

Antimicrobial or Bacteriostatic Agent

The TMC of the invention can also be used as an antimicrobial or bacteriostatic agent in various products, including personal care, cosmetic, pharmaceutical or cosmeceutical products, including but not being limited to those described above, and products for wound treatment.

The formulation of creams and gels typically requires the addition of synthetic parabens as antimicrobial agent for example in cosmetics and dermatological products, including products destined to promote healing of wounds. This is especially true of products that are for repeated use (out of a single container) for a period of time. The compound of the invention can be used as a natural bacteriostatic agent (antimicrobial agent) in such products.

Further, as environmental regulations become more restrictive, the industry has to use antimicrobial preservatives with lesser impact on the environment. The compound of the invention will be very advantageous in that context.

In addition, the compound of the invention, being a hydrophilic biopolymer, acts as an emollient, which is a desirably property in many products. Particularly, this will allow keeping a treated wound moist, thus promoting the healing process.

The matrix metalloproteinase (MMPs) excess in chronic wounds results in the degradation of extracellular matrix proteins and the inactivation of growth factors relevant to tissue reconstruction. With a certain controlled proportion of non-quaternized amine group, the compound of the invention will regulate the activity of the MMPs that would otherwise disrupt the healing progress through coordination.

Thus, the compound of the invention has a triple action making it very attractive as an antimicrobial (or antibacterial) ingredient in various products, especially in products for the treatment of chronic wounds.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

EXAMPLE 1

Synthesis and Characterization of TMC

In this example, N,N-dimethylchitosan (DMC) is prepared using the Eschweiler-Clarke procedure is described. This is a methylation reaction with formic acid and formaldehyde. As shown below, this methylation procedure possesses the advantage of exclusively methylating amine groups via in situ reduction of an imine group. The Eschweiler-Clarke procedure allows the replacement of prior art iodomethane for primary and secondary donor.

Then, DMC has been selectively N-methylated to TMC with a DQ of 0.46 using iodomethane and sodium bicarbonate in a DMF/water mixture. As shown in Example 2, this TMC shows sorption efficiency of bile salts comparable to cholestyramine, the most widely used bile acid sequestrant.

Experimental Section

General Information.

High molecular weight chitosan from Nordic shrimp (*Pandalus borealis*) shells with a degree of deacetylation of 95.9% and a viscosity of 157 cps for a 1% acetic acid aqueous solution was purchased from Marinard Biotech Inc. (Gaspé, Canada). Chitosan was mechanically ground down to 0.6 mm before utilization. The water was deionized with a nanopur Diamond system (model D11931) from Barnestead. Sodium glycocholate (NaGC), sodium taurocholate (NaTC), cholestyramine, anhydrous potassium phosphate monobasic (analytical grade), sodium chloride (SigmaUltra grade) and sodium 4-hydroxybenzenesulfonate were obtained from Sigma-Aldrich. Ultrafiltrations were realized with regenerated cellulose filtration membranes (Amicon YM) possessing a cut-off of 30,000 NMWL in a stirred cell bought from Millipore. IR and NMR spectra are recorded respectively from a PerkinElmer model 1600 series IR spectrometer by the KBr method and a Bruker 700 MHz NMR spectrometer. Coupling constants are given in Hertz. Elemental analyses of chitosan derivatives to determine the degree of substitution were performed on a Costech 410 elemental analyzer. Chitosan derivatives-binding capacities were carried out on a Shimadzu HPLC system (model 10A DVP).

Example 1a

Preparation of N,N-dimethylchitosan (DMC)

In a 250 mL round-bottomed flask, a solution of chitosan (2.01 g, 12.5 mmol of glucopyranosyl units) in 88% formic acid (100 mL) was prepared. The viscous yellow solution was treated with a 37% formaldehyde solution (16.6 mL, 0.166 mol) and was heated at 90° C. during 23 h. Caution: Depending on the heating rate, vigorous release of carbon dioxide can be observed. The resulting solution was evaporated to dryness under reduced pressure. The solid was dissolved in water (100 mL) and the pH of this solution was adjusted to 8-9 with addition of 5 M aqueous sodium hydroxide solution. The precipitate was filtered and washed with water (50 mL), ethanol (50 mL) and diethyl ether (50 mL). The solid was finally dried overnight under vacuum. An off-white solid was obtained with a yield of 73% (1.71 g). IR (cm$^{-1}$) 3449 (OH), 2927 and 2881 (CH), 1658, 1481, 1000-1200 (C—O), 851. $^1$H NMR in $D_2O$ of DMC protonated with HCl, δ 5.06 (d, 1H, $^1J_{1,2}$=6.5, H1), 4.20 (t, 1H, J=8.7, H3), 4.08 (t, 1H, J=~7, H4), 3.92 (d, 1H, J=10.4, H6), 3.80 (broad, 1H, H5), 3.73 (d, 1H, J=8.6, H6), 3.36 (t, J=~7, H2), 3.03 (s, 6H, $CH_3$) ppm. $^{13}$C NMR in $D_2O$ of DMC protonated with HCl, δ 95.05 (C1), 75.50 (C4), 74.53 (C5), 68.16 (C3), 67.31 (C6), 60.35 (C2), 41.88 ($CH_3$) ppm.

Example 1b

Preparation of N,N,N-trimethylchitosan (TMC) Iodide with a DQ of 46% in Protonated Form A suspension of DMC (0.400 g, 2.11 mmol of glucopyranosyl units), sodium bicarbonate (0.532 g, 6.33 mmol) and sodium iodide (0.825 g, 5.50 mmol) in 100 mL DMF/water (90/10 v/v) was treated with iodomethane (0.80 mL, 12.8 mmol) and heated at 75° C. during 8 h. Successive additions of iodomethane (0.80 mL, 12.8 mmol) and sodium bicarbonate (0.532 g, 6.33 mmol) was realized after 2, 4 and 6 h. The solution was evaporated and the resulting solid was dissolved in water (75 mL). The solution was ultrafiltered to a volume of 10 mL and washed two times with water (65 mL). The polymeric solution was concentrated (2-3 mL) by evaporation before being precipitated with acetone (40 mL) and diethyl ether (25 mL) mixture. The solid was filtered, washed with diethyl ether (50 mL) and was dried overnight under vacuum. An off-white solid was obtained with a yield of 100% (0.442 g). IR (cm$^{-1}$) 3385 (OH), 2936 and 2879 (CH), 1654, 1473, 900-1200 (C—O). $^1$H NMR in $D_2O$, δ 5.0-5.7 (C1), 3.6-4.6 (glucopyronosyl hydrogens), 3.3 ($CH_3$), 3.04 ($CH_3$), 2.05 (acetyl) ppm.

Example 1c

Synthesis of N,N-dimethylchitosan (DMChitosan)

Chitosan (12 g, deacetylation degree of 90%) was dissolved in 600 mL of an aqueous solution containing 28 mL of acid formic 88%. Formaldehyde (21 mL, 37%) was added to the reaction mixture and then the solution was heated to 70° C. with a heating mantle during 12 hours. The solution was allowed to reach room temperature and the stirred solution was treated with around 300 mL of sodium hydroxide 5N to reach a pH of 11-12. The resulting suspension was filtered and washed with distilled water until the filtrate possesses a pH of 7. The solid was washed with ethanol (25 mL) followed by ethyl ether (25 mL). The white solid was dried at normal atmosphere. The N-DS of N,N-dimethylchitosan is 2.0.

Example 1d

Synthesis of DMC Using Microwave Oven

Chitosan (0.19 g, deacetylation degree of 90%) was dissolved in 9.2 mL of water and 0.45 mL of acid formic 88%. Formaldehyde (0.34 mL, 37%) was added to the reaction mixture. In a Mars microwave system using MarsXpress™ closed vessels from CEM Corporation, the solution was heated to 130° C. during 5 minutes and the temperature was maintained to 130° C. during 10 minutes with a maximum power of 480 W. The solution was then allowed to reach the room temperature. The pH was adjusted between 7-12 with addition of sodium hydroxide 5N. The resulting suspension was filtered and washed with water. The solid was washed with ethanol followed by ethyl ether. The white solid was dried at normal atmosphere. Yield 95%. The N-DS of N,N-dimethylchitosan is 2.0.

Example 1e

Synthesis of TMC Using Microwave Oven (DMCarbonate)

A suspension containing 0.30 g of N,N-dimethylchitosan, 0.59 g of sodium carbonate and 3.0 mL of dimethyl carbonate in 7 mL of methanol/water mixture (1:9) was prepared. In a Mars microwave system using MarsXpress™ closed vessels from CEM Corporation, the suspension was heated to 140° C. during 5 minutes and the temperature was maintained to 140° C. during 10 minutes with a maximum power of 1600 W. The solution was then allowed to reach the room temperature. If necessary, the pH was adjusted between 7-12 with addition of sodium carbonate. The solid was washed with water. The white solid was dried at normal atmosphere. IR spectra show a strong band at 1480 cm$^{-1}$.

Example 1f

Synthesis of TMC Using Microwave Oven (Iodomethane)

A suspension containing 0.30 g of N,N-dimethylchitosan, 0.90 g of sodium carbonate and alkylating agent (3.0 mL of iodomethane) in 7 mL of methanol/water mixture (1:9) was prepared. In a Mars microwave system using MarsXpress™ closed vessels from CEM Corporation, the suspension was heated to 75° C. during 5 minutes and the temperature was maintained to 75° C. during 15 minutes with a maximum power of 1600 W. The solution was then allowed to reach the room temperature. The pH was adjusted between 7-12 with addition of sodium carbonate. The solid was filtered and washed with water. The white solid was dried at normal atmosphere. Quantitative yield, DQ of repetitive units=83%, molecular weight of TMC is higher using the microwave procedure. Alkylation of N,N-dimethylchitosan with dichloromethane as alkylating agent demonstrates that different alkyl halide could be used.

Example 1g

Synthesis of TMC Using Microwave Oven (DMCarbonate)

A suspension containing 0.30 g of N,N-dimethylchitosan and 3.0 mL of dimethyl carbonate was prepared. In a Mars microwave system using MarsXpress™ closed vessels from CEM Corporation, the suspension was heated to 140° C. during 5 minutes and the temperature was maintained to 140° C. during 10 minutes with a maximum power of 1600 W. The solution was then allowed to reach the room temperature. If necessary, the pH was adjusted between 7-12 with addition of sodium carbonate. The solid was washed with water. The white solid was dried at normal atmosphere. Quantitative yield, IR spectra show a strong band at 1480 cm$^{-1}$.

Example 1h

Synthesis of TMC Using Pressure Vessel

A suspension containing 0.30 g of N,N-dimethylchitosan, 0.59 g of $Na_2CO_3$, 0.72 g of NaI, 3.0 mL of dimethylcarbonate, 30 mL of water/methanol mixture (9:1) was prepared in a pressure vessel. A magnetic bar was added in the vessel before closed. A pressure of 100 PSI of nitrogen was added in the vessel. The pressure vessel containing the suspension was heated to 150° C. during 16 h with stirred. The solution was then allowed to reach the room temperature. The resulting suspension was filtered and the solid was washed with water. The solid was washed with ethanol (25 mL) followed by ethyl ether (25 mL). The solid was dried at normal atmosphere. IR spectra show a band at 1480 cm$^{-1}$.

Example 1i

Viscosity Measurements

Viscosity was measured with a Brookfield viscometer model DV-II+ Pro using spindles LV1 to LV3 at 12 rpm. Viscosity of 0.50% (w/v) TMC chloride in water at 25° C. was 4.37 cP and with addition of 0.1% of sodium dodecylsulfate, the viscosity was 6.87 cP. With addition of sodium dodecylsulfate to a TMC aqueous solution, a white opaque suspension was formed with a texture of hand lotion.

Example 1j

Synthesis of N,N-dipropylchitosan Using Microwave Oven

Chitosan (0.19 g, deacetylation degree of 90%) was dissolved in 9.2 mL of water and 0.45 mL of formic acid 88%. 0.30 mL propanal (propionaldehyde) was added to the reaction mixture. In a Mars microwave system using MarsXpress™ closed vessels from CEM Corporation, the solution was heated to 130° C. during 5 minutes and the temperature was maintained to 130° C. during 15 minutes with a maximum power of 1600 W. The solution was then allowed to reach the room temperature. The pH was adjusted between 7-12 with addition of sodium hydroxide 5N. The resulting suspension was filtered and washed with water. The solid was washed with ethanol followed by ethyl ether. The white solid was dried at normal atmosphere.

Results

Syntheses and Characterization

N,N-dimethylchitosan (DMC).

Prior art alkylation of chitosan with iodomethane and a base leads to the formation of a mixture of unsubstituted, mono-, di- and tri-methyl amines. It has here been shown that the Eschweiler-Clarke procedure possesses can be carried out in an aqueous acidic medium where chitosan is soluble and does not alkylate alcohol groups. However, the Eschweiler-Clarke reaction stops to tertiary amine. If TMC is desired, another alkylation reaction must be realized.

DMC was obtained rapidly and with a good yield and degree of N-substitution (N-DS) by reaction with formaldehyde in formic acid solution.

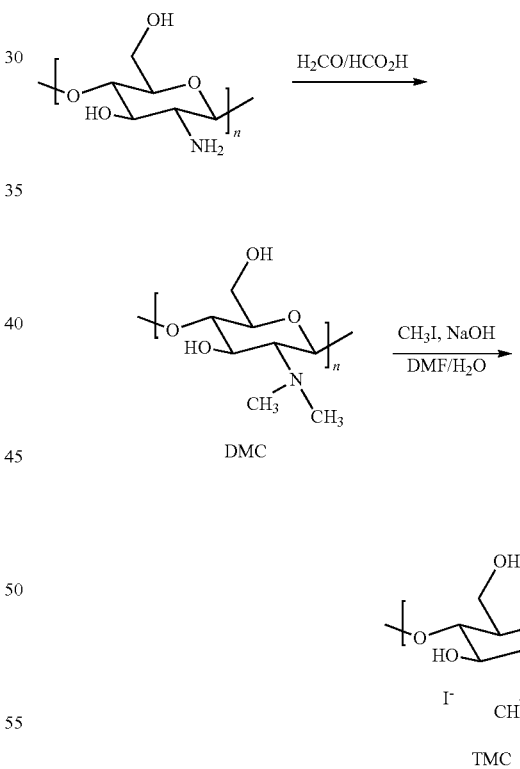

Figure 2:
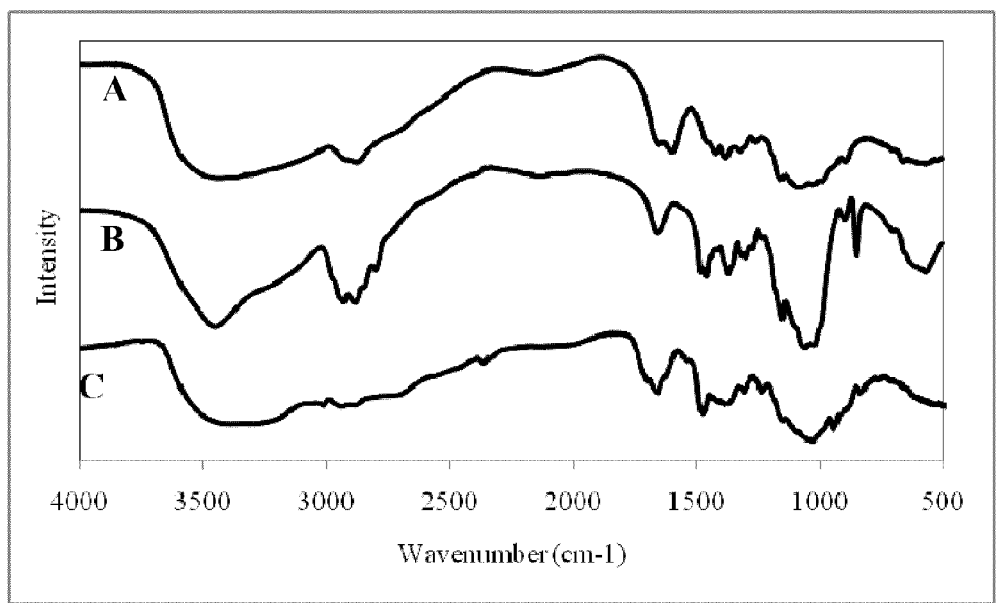
FIG. 2 is the IR spectra of A) chitosan, B) DMC, and C) TMC.

A singlet at 3.1 ppm corresponding to an integration of six protons shows the presence of methyl groups with an excellent DS of 2.0 that is also confirmed in $^{13}C$ NMR by a peak at 41.88 ppm. In the pyranosyl region (3.3-5.3 ppm) of DMC, seven peaks are observed in $^1H$ NMR as shown in FIG. 1. From integration, each of these peaks corresponds to one hydrogen atom. These observations can be explained by different chemical environments for the two hydrogen atoms at C-6 positions that can be explained by hydrogen bonding between $NH(CH_3)_2^+$ and 6-hydroxyl groups. IR spectrum of DMC (FIG. 2) shows a narrower hydroxyl band at 3300 $cm^{-1}$ compared to chitosan and the presence of bands at 2801 and 1481 $cm^{-1}$ attributable to asymmetric C—H stretching and asymmetric $CH_3$ deformation, respectively. DMC is soluble in acidic aqueous solution and it is insoluble in DMSO, ethanol and water.

Reaction of Quaternization with a Weaker Base: Sodium Bicarbonate

The N-dialkylation of chitosan increases the nucleophilicity of nitrogen atoms and facilitates the exhaustive N-methylation that can be achieved in milder reaction conditions. Selective N-methylation of DMC can be realized using a weak base as sodium bicarbonate, sodium carbonate or with sodium hydroxide in a solvent mixture containing a large amount of water, i.e. 50%. Utilization of strong base during reaction of quaternization favors the O-methylation due to partial deprotonation of hydroxyl groups.

Proton NMR of protonated TMC synthesized with sodium bicarbonate reveals two methyl peaks at 3.3 and 3.0 ppm attributable respectively to methyl groups of TMC and DMC. A DQ of 0.46 was obtained after 8 h (95% DD). The DQ was determined from the integral ratio of methyl peak at 3.3 ppm and pyranosyl hydrogen atoms. The IR spectrum of TMC (FIG. 2) shows a strong band at 1480 $cm^{-1}$ corresponding to asymmetric $CH_3$ deformation, that is characteristic of highly N-methylated chitosan salts and N,N,N-trimethylammonium salts. On that point, see Kim C. H., Choi J. W., Chun H. J., Choi K. S., *Polym. Bull.*, 1997, 38, 387; Britto D., Forato L. A., Assis O. B. G., *Carbohydr. Polym.*, 2008, 74, 86-91; Britto D., Assis B. G. O., *Carbohydr. Polym.*, 2007, 69, 305; Britto D., Assis B. G. O., *Intl. J. Biol. Macromol.*, 2007, 41, 198; and Britto D., Campana-Filho S. P., *Polym. Degrad. Stab.*, 2004, 84, 353.

TMC iodide (DQ of 46%) is soluble in water and insoluble in methanol, ethanol, acetone and diethyl ether.

Reaction of Quaternization with a Stronger Base: Sodium Hydroxide

To avoid the protonation of amine groups during the reaction, sodium bicarbonate was replaced by sodium hydroxide, a stronger base. Use of this base in a DMF/water mixture could be used to reach more complete N-alkylation. However, this base favors the O-methylation reaction but utilization of a solvent mixture containing 50% of water prevented this undesired reaction. (On that point, see Polnok A., Borchard G., Verhoef J. C., Sarisuta N., Junginger H. E., *Eur. J. Pharm. Biopharm.*, 2004, 57, 77-83.)

However, tetramethylammonium iodide formed as by-product due to alkylation of dimethylamine that comes from DMF decomposition in alkali medium. The tetramethylammonium iodide, shows strong IR bands at 3012, 1483, 1403, 1396 and 944 $cm^{-1}$, was eliminated by ultrafiltration.

The IR spectrum of TMC synthesized in presence of aqueous sodium hydroxide shows a stronger band at 1483 $cm^{-1}$ compared to the reaction with sodium bicarbonate indicating a higher DQ.

A weak IR band was observed at 1658 $cm^{-1}$ superimposed with the $NH_2$ deformation band on chitosan; it is attributable to the carbonyl stretching of N-acetylglucopyranosyl units.

Conclusion

DMC was obtained with the Eschweiler-Clarke procedure. The Eschweiler-Clarke procedure allows the formation of N,N-dimethylation of chitosan in a simple step with a good yield. NMR spectra of DMC show the coupling constants between the glucopyranosyl hydrogen atoms and the magnetically non equivalence of the hydrogen atoms at C-6 positions. We have demonstrated that DMC is a useful reagent for the TMC synthesis. Selective N-alkylation in presence of a weak base allowed the quaternization of 46% of dimethylamine groups. Water-soluble TMC with DQ up to 46% was indeed synthesized by selective N-methylation with iodomethane in a DMF/water mixture.

EXAMPLE 2

In Vitro Binding to Bile Acids

The TMC of Example 1 was used.

Experimental Section

The reagents used are the same as in Example 1 as set forth above.

Binding of Bile Salts.

In an Erlenmeyer of 25 mL, a mixture containing of 15 mM sodium chloride aqueous solution filtered on a 0.2 μm filter and the substrate (10 mg) was incubated at 37° C. during 40 min. Aqueous solution of NaGC (100 mM) or NaTC (100 mM) was then added and the mixture of 10 mL was stirred on an orbital shaker (Thermoforma, model 420) at 170 rpm during 1 h at 37° C. An aliquot of 1 mL was filtered through a 0.2 μm filter and the solution content was analyzed by HPLC.

HPLC Quantification of Bile Salts.

An Agilent C-18 Sorbax OSD column (4.6×250 mm, 5 μm) was used for quantification of bile salts by HPLC. The mobile phase was a mixture of 0.04 M aqueous potassium hydrogenophosphate filtered on a 0.2 μm filter and acetonitrile (62/38 v/v) at a temperature of 25° C. and a flow rate of 0.7 mL/min. The wavelength of UV-visible detection was set at 200 nm. Sodium 4-hydroxybenzenesulfonate was used as internal standard. The injection volume was 20 μL.

Results

Binding of bile acids with modified chitosan was determined by the variation of concentration in HPLC with the addition of chitosan derivatives. Binding experimental conditions are adapted from reported methods for other chitosan derivatives. On that point, see Lee J. K., Kim S. U., Kim J. H., *Biosci. Biotechnol. Biochem.*, 1999, 63, 833 and Lee J. K., Kim S. Y., Kim S. U., Kim J. H., *Biotechnol. Appl. Biochem.*, 2002, 35, 181. The N,N-dimethylation of chitosan slightly increases the quantity of bound bile salts compared to the parent chitosan.

Cholestyramine sorption saturates rapidly (e.g. inside 10 min). See Lee J. K., Kim S. U., Kim J. H., *Biosci. Biotechnol. Biochem.*, 1999, 63, 833 and Lee J. K., Kim S. Y., Kim S. U., Kim J. H., *Biotechnol. Appl. Biochem.*, 2002, 35, 181.

Figure 3:
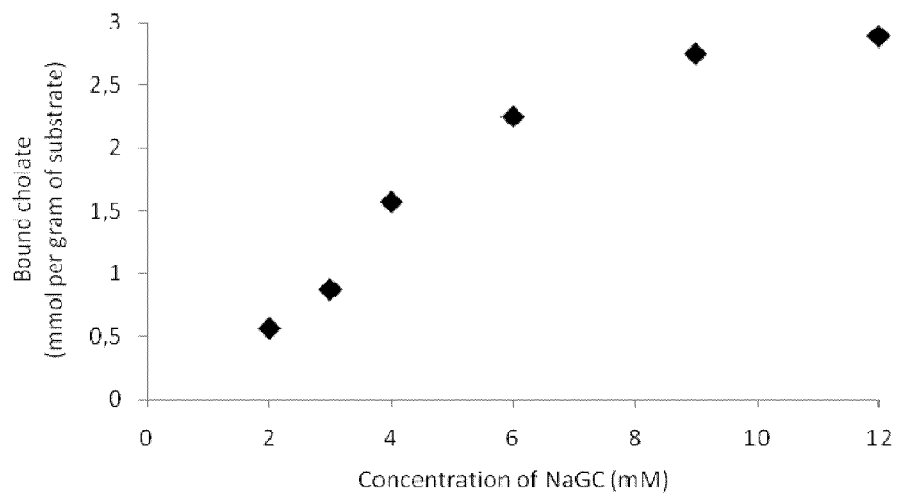
FIG. 3 is the sorption isotherm of NaGC by TMC.

In the case of TMC iodide, a white precipitate appears almost instantaneously when NaGC and TMC aqueous solutions are mixed together. FIG. 3 shows the sorption isotherm of TMC. The sorption saturates at 9 mmol and bound a maximum of 2.89 mmol of cholate compared to the Cholestol and cholestyramine sorption saturate respectively at 1.41 mmol and 3.16 mmol (Table 1). The quantity of bound NaGC per milligram of protonated TMC with a DQ of 46% corresponds to 0.91 molecule of NaGC per glucopyranosyl unit.

TABLE 1

Sorption of NaGC and NaTC by chitosan derivatives and commercial products

| Compounds | [NaGC] (mM) | Bound NaGC (%) | Bound NaGC (mmoles/ g substrate) | [NaTC] (mM) | Bound NaTC (%) | Bound NaTC (mmoles/ g substrate) |
|---|---|---|---|---|---|---|
| chitosan (DD 96%) | 6 | 10 | 0.58 | 2 | 0.1 | 0.00 |
| Cholestol ™ | 1 | 0.0 | 0.00 | — | — | — |
|  | 6 | 18.1 | 1.00 | 2 | 10.0 | 0.19 |
|  | 9 | 14.1 | 1.07 | 3 | 9.7 | 0.34 |
| Cholestyramine | 1 | 82.2 | 0.88 | 1 | 89.4 | 0.66 |
|  | 6 | 35.9 | 1.95 | 2 | 53.9 | 1.21 |
| DMC | 6 | 13.1 | 0.72 | 2 | 1 | 0.02 |
| TMC (DQ = 46%) | 2 | 28.0 | 0.56 |  |  |  |
|  | 3 | 29.0 | 0.87 |  |  |  |
|  | 4 | 39.2 | 1.57 |  |  |  |
|  | 6 | 44.1 | 2.25 |  |  |  |
|  | 9 | 34.6 | 2.75 |  |  |  |
|  | 12 | 28.4 | 2.89 |  |  |  |
| TMC (DQ = 38%)* | 6 | 38.2 | 2.18 | 2 | 34.1 | 0.72 |

*See TMC #115 in Example 3 below

Conclusion

TMC was found to be a fast and an effective bile acid sequestrant due to electrostatic interactions and its solubility in water. In fact, TMC iodide binds NaGC with an efficacy similar to cholestyramine, a protonated synthetic resin.

EXAMPLE 3

Synthesis of TMCs with higher DQs

Example 1 reports inter alia a convenient and efficient procedure for the synthesis of N,N-dimethylchitosan (DMC) in an excellent yield. This procedure involves the N-alkylation of chitosan using the Eschweiler-Clarke reaction in a formic acid/water mixture.

The present example describes the selective and efficacious quaternization of this DMC in various conditions.

Preparation of N,N,N-trimethylchitosan (TMC) iodide with a DQ of 75% (140)

A suspension of DMC (0.600 g, 3.17 mmol of glucopyranosyl units) and sodium iodide (1.23 g, 8.20 mmol) in 100 mL of water/methanol (90/10 v/v) was treated with iodomethane (1.20 mL, 19.3 mmol) and sodium hydroxide solution (0.388 g, 9.7 mmol) and heated at 55-60° C. during 24 h and at 70-75° C. during 48 h. Successive additions of iodomethane (1.20 mL, 19.3 mmol) were carried out after 2, 4, 6, 22, 24, 26 and 28 h. The solution was ultrafiltered to a volume of 10 mL and washed two times with water (90 mL). The polymeric solution was concentrated (2-3 mL) by evaporation before being precipitated with acetone (40 mL) and diethyl ether (25 mL) mixture. The solid was filtered, washed with diethyl ether (50 mL) and was dried overnight under vacuum. An off-white solid was obtained (0.442 g). IR (cm$^{-1}$) 3385 (OH), 2936 and 2879 (CH), 1654, 1473, 900-1200 (C—O). $^1$H NMR in D$_2$O, δ 5.0-5.7 (C1), 3.6-4.6 (glucopyronosyl hydrogens), 3.3 (CH$_3$), 3.04 (CH$_3$), 2.05 (acetyl) ppm.

Preparation of N,N,N-trimethylchitosan (TMC) iodide with a DQ of 95% (146)

A suspension of DMC (0.600 g, 3.17 mmol of glucopyranosyl units) and sodium iodide (1.23 g, 8.20 mmol) in 100 mL of water/methanol (90/10 v/v) was treated with iodomethane (1.20 mL, 19.3 mmol) and sodium carbonate (1.01 g, 9.51 mmol) and heated at 70° C. during 46 h. Successive additions of iodomethane (1.20 mL, 19.3 mmol) were carried out after 2, 4, 6, 22, 24, 26 and 28 h. The suspension was filtered and the solid was washed with water (50 mL), suspended in water (90 mL), ultrafiltered (3×75 mL), acidified with HCl (1 M) during 30 min., brought to pH 8-9 with NaOH (10 M), concentrated by evaporation and finally precipitated with ethanol (75 mL). The solid was filtered, washed with diethyl ether (50 mL) and was dried overnight under vacuum. A light yellow solid was obtained (0.442 g). IR (cm$^{-1}$) 3385 (OH), 2936 and 2879 (CH), 1654, 1473, 900-1200 (C—O). $^1$H NMR in D$_2$O, δ 5.0-5.7 (C1), 3.6-4.6 (glucopyranosyl hydrogens), 3.3 (CH$_3$), 3.04 (CH$_3$), 2.05 (acetyl) ppm.

Preparation of N,N,N-trimethylchitosan (TMC) iodide with a DQ of 90% (149a-f)

A suspension of DMC (10.0 g, 52.9 mmol of glucopyranosyl units) and sodium iodide (20.5 g, 136.5 mmol) in 1.70 L of water/methanol (90/10 v/v) was treated with iodomethane (19.8 mL, 317 mmol) and sodium carbonate (16.8 g, 159 mmol) and heated at 55° C. during 46 h. Successive additions of iodomethane (19.8 mL, 317 mmol) were carried out after 2, 4, 6, 22, 24, 26 and 28 h, and slow addition of 2 eq of sodium carbonate after 6 h and 1 eq at 28 h. The suspension was filtered and the solid was washed with water (200 mL). The solid was poured in 1.7 L HCl 0.5 M, added 1.4 L water and heated to 70-80° C. during 15 min. The solution was concentrated by evaporation until a gel was obtained. The gel was precipitated with ethanol (1.5 L), and the solid was filtered and washed with ethanol. The solid was stirred in diethyl ether (1 L) and was filtered, dried overnight under vacuum. A light yellow solid was obtained with a yield of 90% (10.8 g). IR (cm$^{-1}$) 3385 (OH), 2936 and 2879 (CH), 1654, 1473, 900-1200 (C—O). $^1$H NMR in D$_2$O, δ 5.0-5.7 (C1), 3.6-4.6 (glucopyranosyl hydrogens), 3.3 (CH$_3$), 3.04 (CH$_3$), 2.05 (acetyl) ppm.

The following table summarizes the experimental conditions and the characterization of these and other TMCs.

Note that unless noted otherwise the starting material was DMC and the reactant was iodomethane. In this table, "DQ" is the degree of quaternization, "% of DMC" is the percentage of dimethylated units, "O-DS-3" is the degree of substitution at position 3, "O-DS-6" is the degree of substitution at position 6 and "DA" is the degree of acetylation. Reported values are determined from integration of respective peak compared to those of pyranosyl hydrogen in $^1$H NMR.

It is to be noted that the sum of DQ+% of DMC+DA should be 100%. In most case, it is not exactly 100% because of inherent experimental errors. Therefore, DQ can be estimated using 100%–DA–% DMC. For example, from 146, the DQ is deemed to be very high because only 2+2.6=4.6% of unit are dimethylated or acetylated, which means that 95% of the units are trimethylated.

|  |  |  |  |  | Characterization | | | |
| --- | --- | --- | --- | --- | --- | --- | --- | --- |
| Product # | Solvent | CH$_3$I (Eq.) | Base (3 eq.) | Reaction time | DQ | % of DMC | O-DS-3 | O-DS-6 | DA |
| 55[1] | MeOH | 19.3 | NaHCO$_3$ | 7 to 8 days | 31.1 | 74.3 | 0 | 0 | 3.84 |
| 105a[2] | DMF/H$_2$O (90/10) | 6 | NaHCO$_3$ | 4 h | 35.1 | 76.2 | 0 | 0 | 2.51 |
| 105b[2] | DMF/H$_2$O (90/10) | 6 | NaHCO$_3$ | 8 h | 49.98 | 56.79 | 0 | 0 | 2.51 |
| 115[3] | DMF/H$_2$O (95/5) | 16 | NaHCO$_3$ | 6 h | 38 |  |  |  |  |
| 128[4] qUF | H$_2$O/MeOH (90/10) | 6 | NaOH | 47 h 05 | 83.3 | 46.9 | 73.2 | 44.6 |  |
| 140[5] | H$_2$O/MeOH (90/10) | 6 | NaOH | 46 h 25 | 77 | 10 | 42 | 24 | 3 |
| 146a[6] | H$_2$O/MeOH (90/10) | 6 | Na$_2$CO$_3$ | 21 h 55 | 70 | 14 | 5.7 | 6.4 | 3.4 |
| 146[6] | H$_2$O/MeOH (90/10) | 6 | Na$_2$CO$_3$ | 46 h | 85 | 2 | 8 | 9 | 2.6 |
| 147[7] | DMF/H$_2$O (90/10) | 6 | Na$_2$CO$_3$ | 46 h 30 | 54.7 | 40.9 | — | — | 2.0 |
| 147an[7] | DMF/H$_2$O (90/10) | 6 | Na$_2$CO$_3$ | 24 h | 59.0 | 42.8 | — | — |  |
| 148h[8] | H$_2$O/MeOH (90/10) | 6 | NaOH | 71 h 30 | 89 | 1.8 | 48.4 | 23 | 1.3 |
| 149a-f[9] | H$_2$O/MeOH (90/10) | 6 | Na$_2$CO$_3$ | ~45 h 45 | 85 89 | 10 4 | 8 10 | 6.5 8 | 2 1 |

[1]The quaternization reaction has been carried out on chitosan 100% (DD) rather than DMC. 14.4 eq of NaHCO$_3$ were used, rather than 3. Three additions of CH$_3$I (10.3 eq.) have been carried out during the reaction.
[2]For 105a, 3 eq. NaHCO$_3$ and 6 eq. CH$_3$I were added after 2 hours of reaction. For 105b, 3 eq. NaHCO$_3$ and 6 eq. CH$_3$I were added after 2, 4 et 6 hours of reaction.
[3]3 eq. NaHCO$_3$ and 6 eq. CH$_3$I were added after 2 hours of reaction. Then, after 4 hours of reaction, 6 eq. CH$_3$I were added.
[4]6 eq. CH$_3$I were added after 2, 4, 6, 23, 25, 27 and 29 hours of reaction. NaOH was added as needed to keep the pH of the solution above 7.0. "qUF" means that the product has been purified by ultrafiltration.
[5]No NaI was used. 6 eq. CH$_3$I were added after 2, 4, 6, 23, 25, 27 and 29 hours of reaction. NaOH was added as needed to keep the pH of the solution above 7.0.
[6]6 eq. CH$_3$I were added after 2, 4, 6, 22 h 30, 24 h 30, 26 h 30 and 28 h 30 hours of reaction. NaOH was added as needed to keep the pH of the solution above 7.0.
[7]For 146a, 6 eq. CH$_3$I were added after 2, 4 and 6 hours of reaction. For 146, further additions were made after 22, 24, 26 and 28 hours of reaction. Na$_2$CO$_3$ has been only added after 6 hours of reaction to ensure that the pH would not drop below 7 during the first night. After reaction, the products (146a and 146) were insoluble in water. However, when HCl or NaOH were added to the water, they were soluble. The samples sent for NMR analysis were acidified to eliminate CO$_3^{2-}$. Then, NaOH was added to bring the pH close to 9.
[8]6 eq. CH$_3$I were added after 2, 4, 6, 22, 24, 26 and 28 hours of reaction. Na$_2$CO$_3$ was added as needed to keep the pH of the solution above 7.0. "147an" is 147 (solid) dissolved in water and agitated for on weekend in the presence of CH$_3$COONa (10-15 éq.).
[9]NaOH has not been added at the beginning of the reaction. It was only added as needed to keep the pH of the solution above 7.0. 6 eq. CH$_3$I were added after 2, 4, 6, 22, 24, 26, 28, 46 h 30, 48 h 30, 50 h 30 and 52 h 30 hours of reaction. Product 148 was insoluble in water, and acidified to give 148 h. To acidify it, product 148 was put in water and HCl 12M was added until the product solubilized. Water was then removed by evaporation under vacuum and product 148h was precipitated using methanol.
[10]For 149 a to f, there were 7 iodomethane additions of 6 eq. each. 2 eq. Na$_2$CO$_3$ were added together with the last iodomethane addition of the day and 1 eq. Na$_2$CO$_3$ was added with the last iodomethane addition of the second day. HCl was used to remove CO$_3^{2-}$. The pH was not brought back around 9 using NaOH to avoid forming NaCl, which would complicate purification.

The starting conditions were:

55:

Chitosan (100%) (0.300 g, 1.86 mmol)+NaHCO$_3$ (2.250 g, 26.76 mmol)+CH$_3$I (5.01 g, 36 mmol).

105a and b:

DMC (0.401 g, 2.11 mmol)+NaHCO$_3$ (0.532 g, 6.33 mmol)+NaI (0.825 g, 5.5 mol)+CH$_3$I (1.82 g, 12.8 mmol).

115:

DMC (0.401 g, 2.11 mmol)+NaHCO$_3$ (0.532 g, 6.33 mmol)+NaI (0.825 g, 5.5 mol)+CH$_3$I (4.79 g, 33.7 mmol).

128:

DMC (0.301 g, 1.59 mmol)+NaOH (0.193 g, 4.82 mmol)+NaI (0.618 g, 4.12 mol)+CH$_3$I (1.37 g, 9.63 mmol).

140:

DMC (0.600 g, 3.17 mmol)+NaOH (0.388 g, 9.70 mmol)+NaI (1.23 g, 8.20 mol)+CH$_3$I (2.73 g, 19.3 mmol).

146a and 146:

DMC (0,600 g, 3.17 mmol)+Na$_2$CO$_3$ (1.01 g, 9.51 mmol)+NaI (1.23 g, 8.20 mol)+CH$_3$I (2.73 g, 19.3 mmol).

147:

DMC (0,600 g, 3.17 mmol)+Na$_2$CO$_3$ (1.01 g, 9.51 mmol)+NaI (1.23 g, 8.20 mol)+CH$_3$I (2.73 g, 19.3 mmol).

147an:

DMC (0,600 g, 3.17 mmol)+Na$_2$CO$_3$ (1.01 g, 9.51 mmol)+NaI (1.23 g, 8.20 mol)+CH$_3$I (2.73 g, 19.3 mmol).

EXAMPLE 4

In Vivo Efficacy of TMC as a Bile Acid Sequestrant (BAS)

Totally quaternized TMC chloride was used. This TMC was produced starting from chitosan with DD 90%, which was dimethylated using the Eschweiler-Clarke reaction. Quaternization was then carried out similarly to product #149 above. The DQ was about 89%, i.e. all the available deacetylated units were trimethylated.

1. Context

The purpose of this study was to test the potential of TMC as a hypocholesterolemic agent, using an animal model of lipid disorder. The model used was Golden Syrian hamsters fed a diet rich in saturated fat and cholesterol (0.18%). Hypercholesterolemia was first induced by this rich diet over a period of four weeks. At the end of this period, an analysis of plasma total cholesterol, HDL, and triglycerides as well as body weight measurements were performed. These measurements were used to form three uniform groups of hamsters. Following the formation of these three groups, the treatments were administered over a period of four weeks. The three separate treatments were: negative control treatment (cellulose), a cholesterol-lowering baseline treatment (cholestyramine) and treatment with TMC. These treatments were administered to animals through their food (1%). At the end of the four weeks of treatment, an analysis of plasma total cholesterol, HDL, and triglycerides was performed to determine the hypocholesterolemic potential of TMC.

2 Methodology 2.1 Animals 24 male Syrian golden hamsters of 120-140 g (Charles Rivers, St-Constant, QC) were used for this study. The animals were identified on arrival. A full body assessment was performed on each animal. The body weight of each animal was taken upon arrival and throughout the study at weekly intervals. The animals were acclimated to their environment for 14 days before the start of the study.

2.2 Accommodation

The hamsters were housed two per cage during the period of development of hypercholesterolemia. From the third week of hypercholesterolemia, all hamsters were housed individually. During the study, each cage was covered with a polysulfone filter. The distribution of water ad libitum was provided by a manual system. The food was also provided ad libitum, except during periods of fasting prior to lipid analysis. The cages were clearly identified using a box with a color code according to the groups, also indicating the study number, the group, and the number and sex of the animals.

The room was generally maintained at an ambient temperature of 22±2° C. and a relative humidity of 40±20%. The temperature and humidity of the room were measured daily and recorded. A cycle of light and darkness of 12 hours was provided by an automatic control system and 8-10 air changes per hour were provided by the ventilation system.

For a period of four weeks following the start of treatment, animals were weighed at regular intervals and subjected to a daily physical examination, which ensured the welfare of animals. No adverse symptoms were observed. Only a weight loss in the TMC treated group was noted and is reported in the results section below.

2.3 Diet and Treatments

Standard food kibbles were administered to the animals during the acclimation period. Subsequently, the rich diet in granulated form was administered ad libitum to all animals for a total period of eight weeks. This diet has been used to cause hypercholesterolemia in hamsters. In terms of caloric intake (kcal/g diet), 23% of calories came from protein, 36% from carbohydrates and 41% from fat. The proteins were derived from plant (soybean). Saturated fats came mainly from palm oil and animal fat, then from oil safflower, while polyunsaturated fats were mainly from olive oil and safflower oil. The content of biotin (2 mg/kg), folic acid (10 mg/kg), niacin (37 mg/kg) and pantothenic acid (40 mg/kg) was increased in the diet for all animals compared to the diet recommendations for a hamster. This preventive measure was taken to reduce the risk of vitamin deficiencies in animals receiving TMC. The TMC has a potential affinity for these negatively charged water-soluble vitamins and thus increases the risk of malabsorption.

After four weeks on the rich diet, following the development of hypercholesterolemia, the treatments were incorporated into the diet. To do this, the diet was pulverized using a food processor and the various treatments—microcrystalline cellulose (Sigma-Aldrich Canada Ltd., Oakville, ON), cholestyramine (Sigma-Aldrich Canada Ltd.) and TMC—were incorporated into the diet at a level of 1%. TMC having a certain content of iodide (0.005%), daily intake of iodine for animals treated with TMC was slightly higher at 0.04 mg/kg for an animal which consumed 12 g food per day.

2.4 Cholesterol and Triglycerides Analysis

Analysis of total cholesterol, HDL and triglycerides was performed following the acclimation period (week −4) and four weeks after the start of the rich diet (week 0). These tests were performed firstly to establish if the diet resulted in hypercholesterolemia and secondly, to allow formation of three uniform groups in regard of these parameters. Subsequently, these tests were repeated two and four weeks after starting treatment. The animals were fasted 12 hours before collection of the blood samples required for measuring cholesterol and triglycerides. Collection of these blood samples was performed by intravenous puncture under general anesthesia with isoflurane. Following the plasma preparation, the samples were stored at −80° C. until analysis.

The method used for analyzing plasma lipids (Lemieux C, Gelinas Y, Lalonde J, Labrie F, Cianflone K, Deshaies Y. 2005. Hypolipidemic action of the SERM acolbifene is associated with decreased liver MTP and increased SR-BI and LDL receptors. *J Lipid Res* 46: 1285-94) has been adapted to allow reading microplate using spectrophotometry. The determination of triglycerides and cholesterol was performed using commercial kits from Roche Diagnostics (TG #11877771216 & CHOL #1491458). For each of these kits, Roche Diagnostics ensures linearity of the measurement of triglycerides in plasma for values between 0.05 and 11.3 mmol/L, and for the measurement of cholesterol, for values from 0.08 to 20.70 mmol/L. A standard curve from lyophilized human serum (Roche Diagnostics, #12016630122) was performed for each lipid analysis, both for triglycerides and for cholesterol. We validated our standard curve with a reference "pathological" (PrecipatL®, #11285874-122) supplied by Roche Diagnostics, and which contained high concentrations of triglycerides (3.80 mmol/L with a confidence interval of 3.23 to 4.37) and cholesterol (7.56 mmol/L with a confidence interval of 6.42 to 8.70). This pathological control relatively high in serum lipids also confirms the reliability of the analysis for samples with high fat contents.

2.5 Serum Biochemical Analysis

At the end of the project, a terminal blood sample was collected by cardiac puncture under general anesthesia with isoflurane, as recommended by the Canadian Council on Animal Care (CCAC). The blood was transferred to an Eppendorf tube and then left at room temperature for 30 to 60 minutes to allow coagulation. The tubes were centrifuged at a relative centrifugal force (rcf) of 1500 at 4° C. for ten minutes. The serum portion of each blood sample was then transferred into Eppendorf tubes for subsequent laboratory analysis. Serum biochemical analysis was performed within four hours after sample collection.

2.6 Statistical Analysis

The Student test with a confidence interval of 95% was used to assess the effect of diet on plasma total cholesterol, HDL, non-HDL, HDL/non-HDL ratio, and triglycerides (Prism software). The analysis of variance (ANOVA) with two criteria (time and treatment), with an interval of 95% was used to compare the plasma levels of total cholesterol, HDL, non-HDL, HDL/non-HDL ratio and triglycerides between treatment groups (TMC and cholestyramine) and the control group (cellulose). The post-hoc analysis that was used in this study is the Bonferroni multiple comparison.

3 Results 3.1 Development of Hypercholesterolemia

Table 1 summarizes the results of the lipid analysis obtained before the start of the rich diet and after four weeks of consuming the rich diet.

Figure 4:
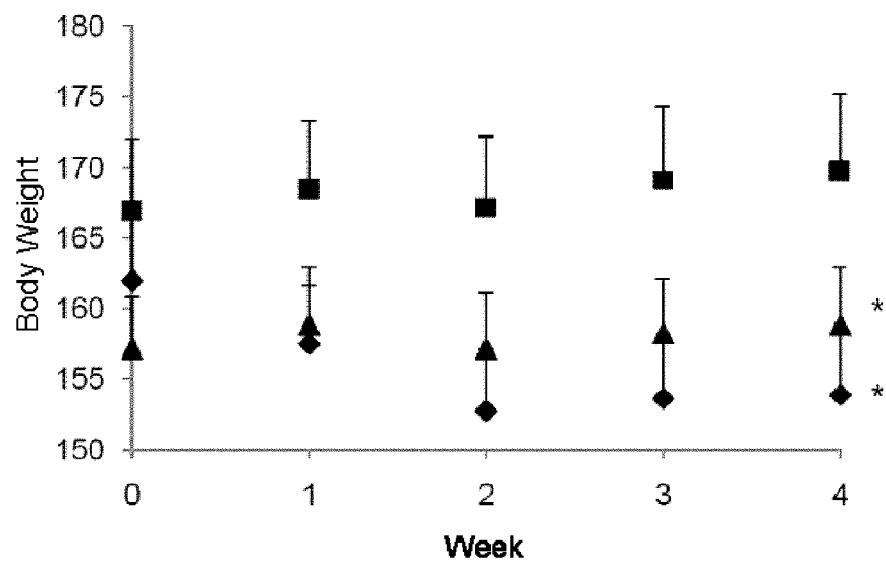
FIG. 4 shows the changes in body weight during the four weeks of treatment with cellulose (squares), TMC (diamonds) and cholestyramine (triangles)

The first week of treatment with TMC, a loss of body weight of 4.25 g on average was observed in hamsters receiving this treatment (FIG. 4). In contrast, the groups that received either cellulose or cholestyramine had a weight gain of 1.50 and 1.75 g, respectively, during the same period. An additional loss of body weight of 4.75 g on average was observed in hamsters receiving the TMC during the second week of treatment (FIG. 4). However, body weight in hamsters of the two other groups was relatively stable. It should be mentioned that the loss of body weight in hamsters receiving the TMC was highly variable from one individual to another, the extremes being 19 g for the hamster that had lost the most body weight within the first two weeks and 1 g for the hamster that has lost the least. Over the next two weeks, body weight of hamsters receiving the TMC has stabilized. Monitoring of food consumption of each group

TABLE 1

Development of high cholesterol

|  | Total cholesterol (mmol/L) | HDL (mmol/L) | NON-HDL (mmol/L) | Ratio | TG (mmol/L) | Body weight (g) |
| --- | --- | --- | --- | --- | --- | --- |
| Before rich diet | 3.13 ± 0.09 | 1.73 ± 0.06 | 1.40 ± 0.06 | 1.30 ± 0.10 | 2.57 ± 0.23 | 141 ± 2 |
| After rich diet | 6.57 ± 0.15* | 3.27 ± 0.07* | 3.30 ± 0.11* | 1.01 ± 0.04* | 6.04 ± 0.31* | 162.3 ± 3* |

All number are averages ± standard error
*$P < 0.05$: significant difference between measurements taken before (week −4) and after the rich diet (week 0) according to the Student's test.

These results demonstrate that the plasma levels of total cholesterol, HDL, non-HDL cholesterol and triglyceride levels have doubled after four weeks of consumption of the diet rich in saturated fat and containing 0.18% cholesterol. In addition, the ratio of HDL/non-HDL cholesterol rose an average of 1.30 to 1.01, reflecting the greater intake of non-HDL compared to HDL.

From these plasma test results performed at the end of four weeks of consuming the rich diet, the distribution of animals was made in order to obtain three hypercholesterolemic groups, with a mean and standard error comparable for each of these parameters (Table 2).

suggests that there is no statistical difference between the group treated with TMC and the control group. A reduction in food consumption in the treated group at TMC does not seem to explain the weight loss associated with this treatment.

The significant difference between body weight of cholestyramine-treated group and the control group (FIG. 4) comes mainly from the initial difference of 9.25 g between these two groups. This difference was not significant in the formation of groups but the ANOVA has achieved the level of significance since the gap remained constant throughout

TABLE 2

Forming Uniform Groups

| Group | Total cholesterol (mmol/L) | HDL (mmol/L) | NON-HDL (mmol/L) | Ratio | TG (mmol/L) | Body weight (g) |
| --- | --- | --- | --- | --- | --- | --- |
| Cellulose | 6.58 ± 0.24 | 3.25 ± 0.14 | 3.32 ± 0.16 | 0.99 ± 0.16 | 6.08 ± 0.48 | 166.75 ± 5.06 |
| TMC | 6.60 ± 0.26 | 3.26 ± 0.02 | 3.34 ± 0.19 | 0.99 ± 0.05 | 6.17 ± 0.46 | 162.00 ± 4.36 |
| Cholestyramine | 6.54 ± 0.29 | 3.30 ± 0.14 | 3.24 ± 0.25 | 1.05 ± 0.25 | 5.87 ± 0.71 | 157.50 ± 3.74 |

All number are averages ± standard error 3.2 Effects of TMC and cholestyramine

Throughout the study, body weight was measured each week and food consumption was estimated at the same frequency for each hamster. These results are shown in FIG. 4 showing the changes in body weight during the four weeks of treatment with cellulose (square), TMC (diamond) or cholestyramine (triangle). In this figure, * means $P<0.05$: significant difference between treated groups and control groups, irrespective of the time, according to ANOVA 2 criteria of classification.

the four weeks of treatment. When statistically analyzing the weight gain between groups, no significant difference between the group treated with cholestyramine and the control group is apparent.

Figure 5:
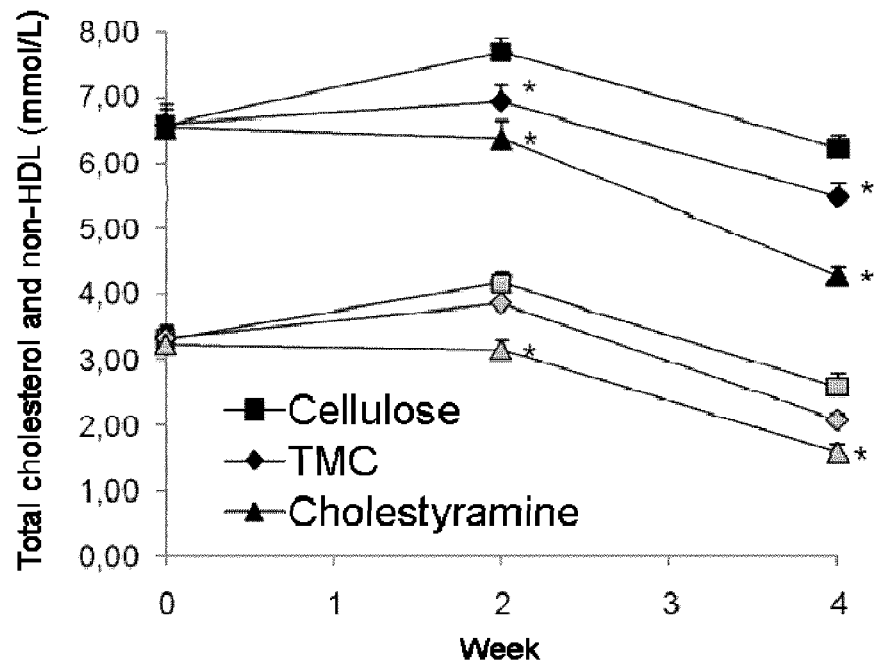
FIG. 5 shows the total cholesterol (black symbols) and plasma non-HDL (VLDL, LDL and MDL—gray symbols) during the four weeks of treatment with cellulose (squares), TMC (diamonds) and cholestyramine (triangles)
Figure 6:
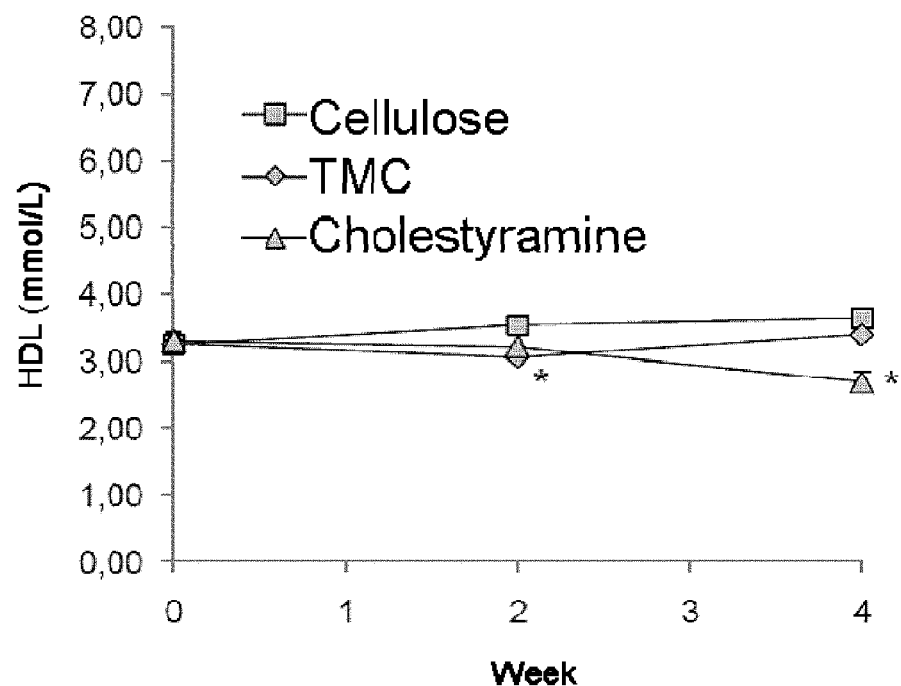
FIG. 6 shows the changes in HDL during the four weeks of treatment with cellulose (squares), TMC (diamonds) and cholestyramine (triangles)

The test results relating to plasma total cholesterol and non-HDL and HDL are presented in FIGS. 5 and 6, respectively.

Total cholesterol (black symbols) and plasma non-HDL (VLDL, LDL and MDL—gray symbols) during the four weeks of treatment with cellulose (square), TMC (diamond)

or cholestyramine (triangle) are shown in FIG. 5. In this figure, * means P<0.05: significant difference between treated groups and the control group at weeks indicated by post-hoc analysis of Bonferroni. This figure shows that total cholesterol and non-HDL follows about the same trend for all treatment.

Changes in HDL during the four weeks of treatment with cellulose (square), TMC (diamond) or cholestyramine (triangle) are shown in FIG. 6. In this figure, * means P<0.05: significant difference between the TMC treated group and the control group in the second week, then between the group treated with cholestyramine and the control group at the fourth week of treatment, according to the post-hoc analysis Bonferroni.

TMC significantly reduced total cholesterol compared to the control group receiving the cellulose (FIG. 5). At the end of four weeks of treatment, reduction in plasma non-HDL by TMC was 19% (FIG. 5) and that of HDL was 7% (FIG. 6). Thus, although the significance level was not reached, the TMC has improved by 13% the ratio of HDL/non-HDL (FIG. 7) after four weeks of treatment.

Cholestyramine significantly reduced plasma total cholesterol, non-HDL (FIG. 5) and HDL (FIG. 6). Considering the effect of reducing the larger decrease in non-HDL (38%, FIG. 5) than in HDL (26%, FIG. 6), cholestyramine has led to an improvement in the ratio HDL/non-HDL (FIG. 7) but, in a non-significant way.

Figure 7:
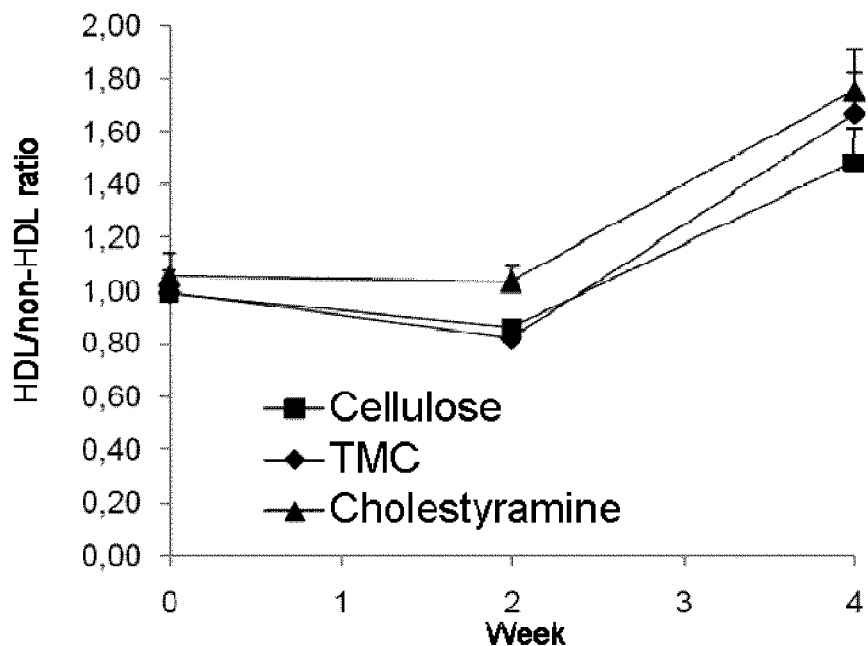
FIG. 7 shows the HDL/non-HDL ratio during the four weeks of treatment with cellulose (squares), TMC (diamonds) and cholestyramine (triangles)

FIG. 7 shows the HDL/non-HDL ratio during the four weeks of treatment with cellulose (square), TMC (diamond) or cholestyramine (triangle).

Figure 8:
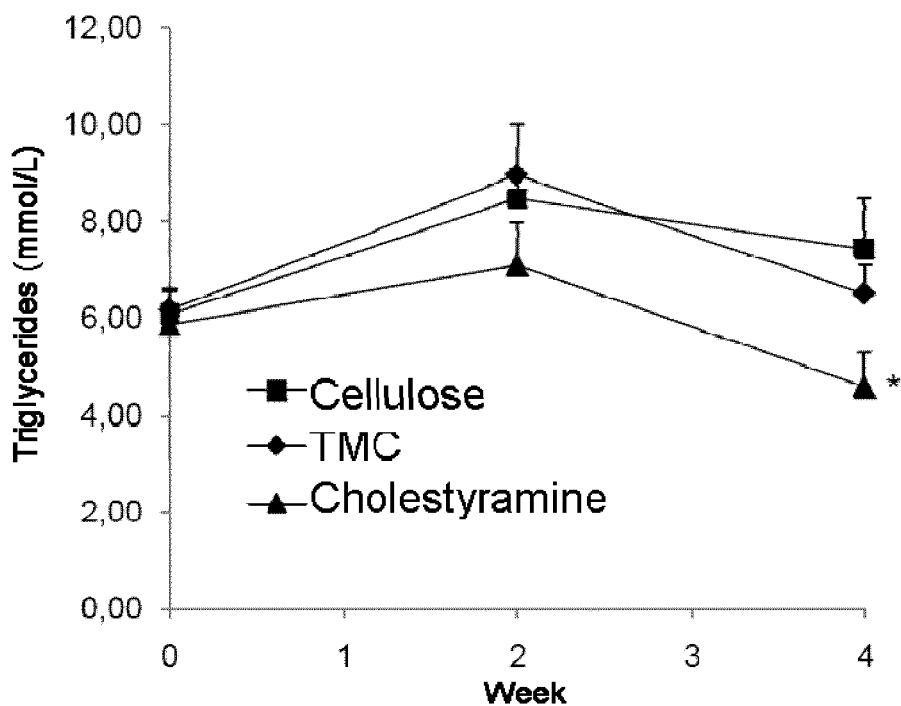
FIG. 8 shows the triglycerides in the four weeks of treatment with cellulose (squares), TMC (diamonds) and cholestyramine (triangles)

At the fourth week of treatment, TMC had caused a non-significant 13% decrease in plasma triglycerides compared with the control group receiving the cellulose (FIG. 8). In comparison, cholestyramine caused a significant decrease of 38% in plasma triglycerides compared with the control group (FIG. 8).

FIG. 8 shows the triglycerides in the four weeks of treatment with cellulose (square), TMC (diamond) and cholestyramine (triangle). In this figure, * means P<0.05 between the group treated with cholestyramine and the control group at the fourth week of treatment, according to the analysis post hoc Bonferroni.

The purpose of this study was to test the potential of TMC as a hypocholesterolemic agent, using an animal model for lipid disorder. TMC is a bile acids sequestrant, which cause their elimination in the feces. By binding bile acids, it prevents their enterohepatic reabsorption. The main precursor of bile acids is cholesterol, much of which is normally recovered when bile acids are reabsorbed in the intestine and returned to the liver via the circulation. Bile acid binding resins such as cholestyramine, also inhibit the reabsorption of bile acids. The excretion of bile salts is then increased tenfold. This leads to an increased production of bile acids by the liver resulting in a loss of cholesterol. This has the effect of increasing LDL receptor activity. The net result is a decrease in plasma LDL of about 10 to 35%. Since these bile acids binding agents are not absorbed, no significant systemic effect is associated with them.

One of the possible side effects of TMC is vitamin deficiency. This is associated with the affinity of TMC for certain negatively charged water-soluble vitamins. To investigate the hypocholesterolemic effect of TMC while preventing such side effects, the levels of certain vitamins in the rich diet was increased (Section 2.3). Since an excess of these vitamins may have affect health and plasma cholesterol (see Luria M H. 1988. Effect of low-dose niacin on high-density lipoprotein cholesterol and total cholesterol/high-density lipoprotein cholesterol ratio. Arch Intern Med 148: 2493-5 and Johansson J, Carlson L A. 1990 The effects of nicotinic acid treatment on high density lipoprotein particle size subclass levels in hyperlipidaemic subjects. Atherosclerosis 83: 207-16), the vitamin supplement was limited to avoid side effects. Furthermore, all the animals received this diet containing a higher level of vitamins so as to avoid bias between the three groups.

The nutrients contained in the hypercholesterolemic diet were also subject to a thorough screening process. We needed to establish a diet aimed at developing a model of lipid disorder in hamsters, while considering that the model can reproduce approximately the conditions found in humans. The animal model of lipid disorder developed initially involved the consumption of a diet whose main protein was casein. Casein contributes to a more severe increase in plasma cholesterol compared to soy protein and, according to some authors, the content of vegetable rather than animal protein contributes to reduced elimination of sterols, alterations of the expression of certain receptors involved in lipoprotein metabolism, etc. (See Beynen A C, West C E, Van Raaij J M, Katan M B. 1984. Dietary soybean protein and serum cholesterol. Am J Clin Nutr 39: 840-1; Fernandez M L, Wilson T A, Conde K, Vergara-Jimenez M, Nicolosi R J. 1999. Hamsters and guinea pigs differ in their plasma lipoprotein cholesterol distribution when fed diets varying in animal protein, soluble fiber, or cholesterol content. J Nutr 129: 1323-32; Terpstra A H, Holmes J C, Nicolosi R J. 1991. The hypocholesterolemic effect of dietary soybean protein vs. casein in hamsters fed cholesterol-free or cholesterol-enriched semipurified diets. J Nutr 121: 944-7; and Beynen A C. 1990. Comparison of the mechanisms proposed to explain the hypocholesterolemic effect of soybean protein versus casein in experimental animals. J Nutr Sci Vitaminol (Tokyo) 36 Suppl 2: S87-93).

The high interindividual variation caused by the combination of animal protein and cholesterol compared to that observed by the combination of vegetable protein and cholesterol (Terpstra A H, Holmes J C, Nicolosi R J. 1991. The hypocholesterolemic effect of dietary soybean protein vs. casein in hamsters fed cholesterol-free or cholesterol-enriched semipurified diets. J Nutr 121: 944-7) prompted us to opt for this second alternative. In addition, studies in hamsters in which cholestyramine was used as positive control were performed with diets containing the soy bean protein source (see Wilson T A, Nicolosi R J, Rogers E J, Sacchiero R, Goldberg D J. 1998. Studies of cholesterol and bile acid metabolism, and early atherogenesis in hamsters fed GT16-239, a novel bile acid sequestrant (BAS). Atherosclerosis 140: 315-24 and Daggy B P, O'Connell N C, Jerdack G R, Stinson B A, Setchell K D. 1997. Additive hypocholesterolemic effect of psyllium and cholestyramine in the hamster: influence on fecal sterol and bile acid profiles. J Lipid Res 38: 491-502). Regarding the amount of cholesterol present in the normal diet of humans, the level is around 100-300 mg/1000 kilocalories consumed. The level of dietary cholesterol content in the diet prepared for the current project was 406 mg/1000 kilocalories consumed. As for the content of the diet in fat, it was 20% in weight (g) or 41% in terms of caloric intake (Section 2.3), fat having a caloric intake (kcal/g) higher than that of carbohydrates or proteins. The main source of saturated fat contained in the chosen rich diet was palm oil and animal fat and then safflower oil, while unsaturated fats came from olive oil and safflower oil. The combination of saturated fat and cholesterol in the hypercholesterolemic diet reproduced quite well a rich diet consumed by the human population and ensured that the plasma cholesterol levels would significantly increase in hamsters fed this diet (Fernandez M L, Wilson T A, Conde K, Vergara-Jimenez M, Nicolosi R J. 1999. Hamsters and guinea pigs differ in their plasma lipoprotein cholesterol distribution when fed diets varying in animal protein, soluble fiber, or cholesterol content. *J Nutr* 129: 1323-32).

TMC, administered at a level of 1% in the diet for four weeks showed a hypocholesterolemic effect on total cholesterol level. HDL decreased slightly (7%) by treatment with TMC while non-HDL cholesterol was more significantly reduced (19%), which had the effect of promoting a better ratio HDL/non-HDL. The effect of the most sought after cholesterol-lowering therapy is to lower non-HDL cholesterol without affecting HDL. Therefore, the fact that the TMC resulted in a greater reduction of non-HDL compared to HDL is positive. TMC does not seem to affect the plasma levels of triglycerides.

Cholestyramine, an already marketed hypocholesterolemic drug, served as positive control in this study. It caused a significant reduction in plasma total cholesterol, non-HDL and HDL. It reduced the level of non-HDL (38%) more than the levels of HDL (26%), and thus improved the HDL/non-HDL ratio in a manner comparable to TMC. The reduction in total cholesterol was higher with cholestyramine than with TMC. Moreover, the level of plasma triglycerides was significantly reduced by cholestyramine. The results we obtained with cholestyramine in hamsters corroborate those reported by other authors (Wilson T A, Nicolosi R J, Rogers E J, Sacchiero R, Goldberg D J. 1998. Studies of cholesterol and bile acid metabolism, and early atherogenesis in hamsters fed GT16-239, a novel bile acid sequestrant (BAS). *Atherosclerosis* 140: 315-24 and Nicolosi R J, Wilson T A, Krause B R. 1998. The ACAT inhibitor, CI-1011 is effective in the prevention and regression of aortic fatty streak area in hamsters. *Atherosclerosis* 137: 77-85).

At the end of in vivo experiment, blood tests on hamsters (TMC treated and negative control) were performed. These tests include the concentration in albumin, ALT (SGPT), ALT (SGOT), total bilirubin, CK, creatinine, gamma-GT (GGT), glucose, total protein, A/G ratio, urea nitrogen (BUN) and globulin. Results between these two groups of hamsters were similar.

EXAMPLE 5

TMC Antimicrobial Effect

Figure 9:
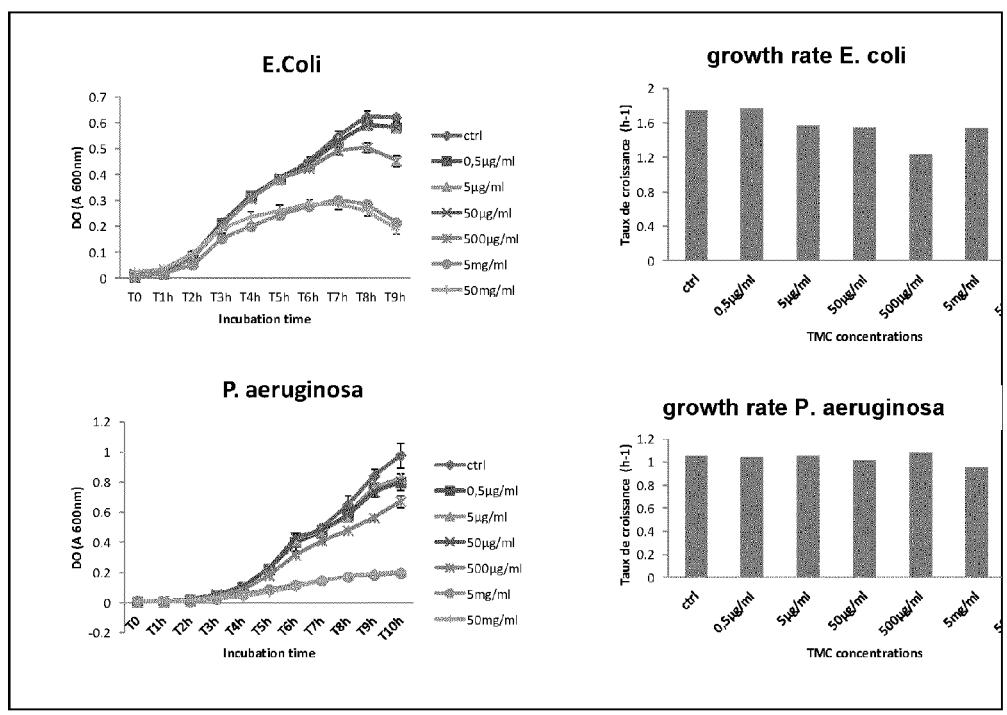
FIG. 9 shows growth evolution and rate of growth for gram negative bacteria *E. coli* and *P. aeruginosa* based on the TMC concentration.
Figure 10:
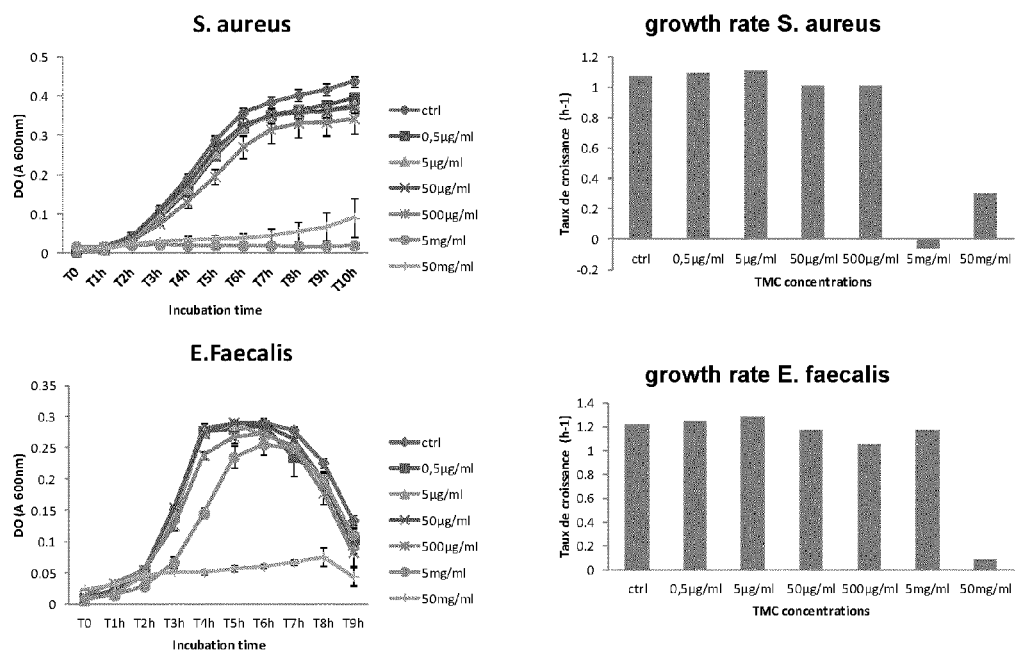
FIG. 10 shows growth evolution and rate of growth for gram positive bacteria *S. aureus* and *E. faecalis* based on the TMC concentration.
Figure 11:
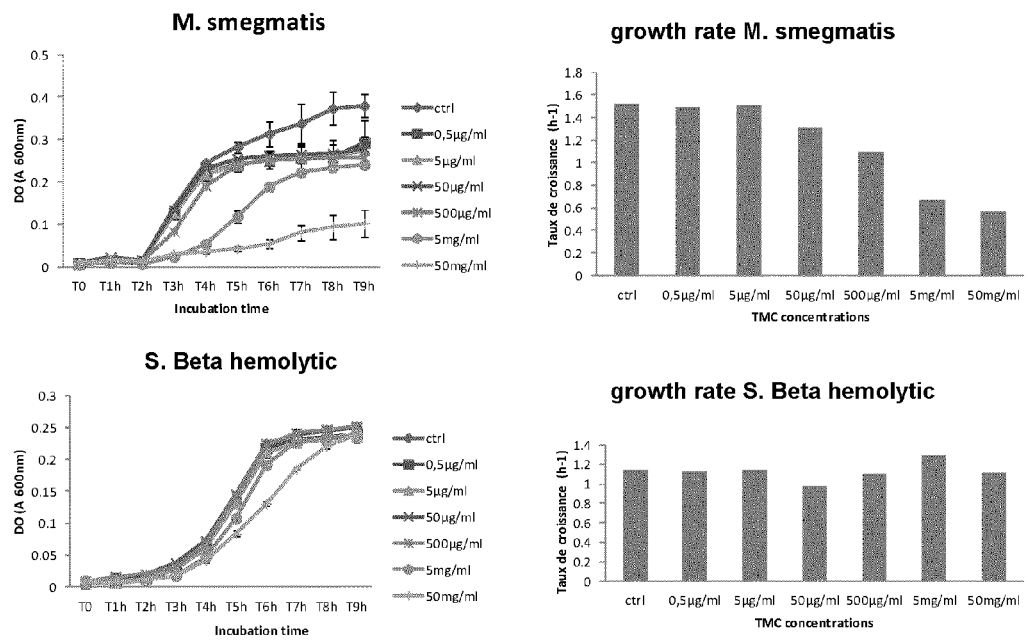
FIG. 11 shows growth evolution and rate of growth for gram positive bacteria *M. smegmatis* and *S. beta hemolitic* based on the TMC concentration.

Antimocrobial effect of TMC was assessed at six different concentrations (0.5 µg, 5 µg, 50 µg, 500 µg, 5 mg et 50 mg/mL) on gram negative bacteria *Escherichia coli* and *Pseudomonas aeruginosa* and gram positive bacteria *Enterococcus faecalis, Staphylococcus aureus, Streptococcus* beta hemolytic and *Mycobacterium smegmatis*. The experiments were monitored by spectrophotometry at an absorbance of 600 nm. FIGS. 9-11 outline the results obtained.

Experimental Conditions

Preparation of TMC Solution 0.3006 g of TMC was dissolved into 6 mL of physiological water to obtain a stock solution at 50 mg/mL. The stock solution was then diluted by a factor of 10 to obtain a solution at 5 mg/mL (600 µL of stock solution+5.4 mL physiological water). The 5 mg/mL solution was further diluted by a factor of 10. The process was repeated until a 0.5 µg/mL solution was obtained.

Preparation of the Different Bacterial Strains Used:

Each strain was transplanted in a nutrient broth Luria Bertani (LB) previously autoclaved. Transplantation was performed as follows: 100 µL of strain in 10 mL of LB, incubation in an oven at 35° C. between 12 and 24 hours, measurement of the optical density (OD) at an absorbance of 600 nm.

Experiment on Microphages:

Each strain is first transplanted into LB in order to work on fresh strains in growing phase. An OD measurement is performed at an absorbance of 600 nm. Based on the OD obtained, the solution is diluted by a factor X in order to obtain a final OD close to 1.0 (working solution).

TABLE 3

| | | | Ctrl | | | | | | | | |
|---|---|---|---|---|---|---|---|---|---|---|---|
| | 1 0.5 µg/ml | 2 5 µg/ml | 3 50 µg/ml | 4 500 µg/ml | 5 5 mg/ml | 6 50 mg/ml | 7 | 8 | 9 | 10 | 11 | 12 |
| A R1 | | | | | | | | | | | Ctrl- | |
| B R2 | | | | | | | | | | | Ctrl- | |
| C R3 | | | | | | | | | | | Ctrl- | |
| D | | | | | | | | | | | | |
| E | | | | | | | | | | | | |
| F | | | | | | | | | | | | |
| G | | | | | | | | | | | | |
| H | | | | | | | | | | | Blank | blank | blank |

Total volume in each well: V = 200 µL

Blank: 180 µL of LB + 20 µL of physiological water

Control: 160 µL of LB + 20 µL of strain + 20 µL of physiological water

[TMC]: for each concentration: 160 µL of LB + 20 µL of strain + 20 µL of TMC solution Control: 200 µL of LB An OD is performed at the beginning of the experiment (T0), then the whole experimental system is incubated at 35° C. in an oven. The OD is measured every hour until the stationary phase is reached. Before each measurement, the experimental medium is homogenized (using a 750 rpm microplate). Each measurement is performed three times.

For each strain, results are presented as graphs showing the OD evolution versus incubation time for each TMC concentration: OD=F(t). The growth rate is subsequently calculated using the following formula: $\mu=(\log Nt-\log N0)/(0.301*t)$.

Results

The results are outlined in FIGS. 9-11. As can be seen in FIG. 9, the effect of TMC is similar for all strains. The growth rates of *E. coli* and *P. aeruginosa*, although still high, decrease slightly as the TMC concentration increases. The maximum growth, reached for the two highest TMC concentrations (5 and 50 mg/mL), is significantly lower than for the control. These results suggest that TMC has a bacteriostatic effect, i.e. TMC at concentrations higher than or equal to 5 mg/mL limits bacteria multiplication. A similar activity is noted for TMC at a concentration of 500 µg/mL. The maximum growth is indeed significantly lower than for the control. However, TMC bacteriostatic effect at this concentration is significantly lower than for TMC at higher concentrations (5 and 50 mg/mL). It is noted that for TMC concentrations below 500 µg/mL, no relevant effect on the growth of the two strains is observed.

FIGS. 10 and 11 show the results obtained for the gram positive bacteria. Results obtained for *S. aureus* and *E. faecalis* (FIG. 10) suggest a bactericidal effect for TMC at higher concentrations. Growth rate are indeed low and growth remains below 0.1 for TMC concentrations higher than or equal to 5 mg/mL for *S. aureus* and above 50 mg/mL for *E. faecalis*.

The TMC effect on the growth of *M. smegmatis* (FIG. 11) is similar to the effect on the two gram negative strains *E. coli* and *P. aeruginosa*. Despite a positive growth, the maximum growth, reached for the two highest concentrations (5 and 50 mg/mL), is significantly lower than for the control and for the other concentrations, which also suggests a bacteriostatic effect for TMC at these two concentrations.

Regarding strain *S. hemolytic*, TMC does not appear to have any effect on the growth of this strain despite a slight difference with the control at a concentration of 50 mg/mL.

Based on the above results, TMC appears to have (i) a bacteriostatic effect (limiting effect) on the growth of most of the strains studied, at concentrations higher than or equal to 5 mg/mL, and (ii) a bactericidal effect on certain strains at concentrations higher than or equal to 5 mg/mL.

Although the present invention has been described hereinabove by way of specific embodiments thereof, it can be modified, without departing from the spirit and nature of the subject invention as defined in the appended claims.

REFERENCES

The following documents are herein incorporated by reference in their entirety:

Avadi M. R., Zohuriaan-Mehr M. J., Younessi P., Amini M., Rafiee Tehrani M., Shafiee A., *J. Bioact. Compat. Polym.*, 2003, 18, 469.

Bayat A., Sadeghi A. M. M., Avadi M. R., Amini M., Rafiee-Tehrani M., Shafiee A., Majlesi R., Junginger H. E., *J. Bioact. Compat. Polym.*, 2006, 21, 433.

Beynen A C, West C E, Van Raaij J M, Katan M B. 1984. Dietary soybean protein and serum cholesterol. Am J Clin Nutr 39: 840-1

Beynen A C. 1990. Comparison of the mechanisms proposed to explain the hypocholesterolemic effect of soybean protein versus casein in experimental animals. J Nutr Sci Vitaminol (Tokyo) 36 Suppl 2: S87-93

Biopolymers, Vol. 6: Polysaccharides II: Polysaccharides from Eukaryotes, Vandamme E. J., De Baets S., Steinbüchel A., Wiley-VCH, New York, 2002, p. 488.

Borchard G., *Adv. Drug Delivery Rev.*, 2001, 52, 145.

Britto D., Assis B. G. O., *Carbohydr. Polym.*, 2007, 69, 305.

Britto D., Assis B. G. O., *Intl. J. Biol. Macromol.*, 2007, 41, 198.

Britto D., Campana-Filho S. P., *Polym. Degrad. Stab.*, 2004, 84, 353.

Britto D., Forato L. A., Assis O. B. G., *Carbohydr. Polym.*, 2008, 74, 86-91.

Cafaggi S., Russo E., Stefani R., Leardi R., Caviglioli G., Parodi B., Bignardi G., Totero D., Aiello C., Viale M., *J. Control. Release*, 2007, 121, 110-123.

Cationic cellulosic polymers with multifunctional and outstanding performance for personal care, www.dow.com, on May 19, 2010.

Clarke J., Robbins C. R., Reich C., Journal of the society of cosmetic chemists, 1991, 42, 341.

Cumming J. L., Hawker D. W., Nugent K. W., Chapman H. F., Journal of Environmental Science and Health Part A, 2008, 43, 113.

Curti E., Britto D., Campana-Filho S. P., *Macromol. Biosci.*, 2003, 3, 571-576.

Daggy B P, O'Connell N C, Jerdack G R, Stinson B A, Setchell K D. 1997. Additive hypocholesterolemic effect of psyllium and cholestyramine in the hamster: influence on fecal sterol and bile acid profiles. J Lipid Res 38: 491-502

Di Colo G., Burgalassi S., Zambito Y., Monti D., Chetoni P., J. Pharm. Sci., 2004, 93, 2851-2862.

Dodane, V. et al. "Effect of chitosan on epithelial permeability and structure," Int. J. Pharm. May 10, 1999; 182(1):21-32.

Dodou D., Breedveld P., Wiering a P. A., Euro. J. Pharm. Biopharm., 2005, 60, 1.

Drovetskaya T. V., Kreeger R. L., Amos J. L., Davis C. B., Zhou S., Journal of Cosmetic Science, 2004, 55, S195.

Dung P., Milas M., Rinaudo M., Desbrieres J., *Carbohydr. Polym.*, 1994, 24, 209-214.

El-Sharif, A. A. et al. Curr. Microbiol., 2011, 62, 739-745.

Fernandez M L, Wilson T A, Conde K, Vergara-Jimenez M, Nicolosi R J. 1999. Hamsters and guinea pigs differ in their plasma lipoprotein cholesterol distribution when fed diets varying in animal protein, soluble fiber, or cholesterol content. J Nutr 129: 1323-32

Florea B. I., Thanou M., Junginger H. E., Borchard G., *J. Control. Release*, 2006, 110, 353.

Gruber J. V., Journal of Cosmetic Science, 2009, 60, 385.

Hamman J. H., Kotzé A. F., *Drug Dev. Ind. Pharm.*, 2001, 27, 373-380.

Hamman J. H., Stander M., Junginger H. E., Kotzé A. F., *S. T. P. Pharma Sci.*, 2000, 10, 35.

Harding J. R., Jones J. R., Lu S.-Y., Wood R., *Tetrahedron Lett.*, 2002, 43, 9487-9488.

Illum, L. et al. "Chitosan as a novel nasal delivery system for peptide drugs," Pharm. Res. August 1994; 11(8):1186-9.

Jia Z., Shen D., Xu W., *Carbohydr. Res.*, 2001, 333, 1.

Johansson J, Carlson L A. 1990. The effects of nicotinic acid treatment on high density lipoprotein particle size subclass levels in hyperlipidaemic subjects. Atherosclerosis 83: 207-16

Kean T., Roth S., Thanou M., *J. Control. Release*, 2005, 103, 643.

Kenawy, E. et al. Biomacromolecules, 2007, 8, 1359-1384.

Kim C. H., Choi J. W., Chun H. J., Choi K. S., *Polym. Bull.*, 1997, 38, 387.

Kotzé A. F., LuepEn H. L., Leeuw B. J., Boer B. G., Verhoef J. C., Junginger H. E., *Pharmaceutical Research*, 1997, 14, 1197.

Kotzé A. F., Thanou M., Lueben H. L., de Boer A. G., Verhoef J. C., Junginger H. E., *Eur. J. Pharm. Biopharm.*, 1999, 47, 269.

Le Berre A., Delacroix A., Bull. Soc. Chim. France, 1976, 640, 647.

Lee J. K., Kim S. U., Kim J. H., *Biosci. Biotechnol. Biochem.*, 1999, 63, 833.

Lee J. K., Kim S. Y., Kim S. U., Kim J. H., *Biotechnol. Appl. Biochem.*, 2002, 35, 181.

Lemieux C, et al. 2005. J Lipid Res 46: 1285-94

Lim, S. H. et al. J. Macromol. Sci.-Polym. Rev., 2003, C43, 223.

Luria M H. 1988. Arch Intern Med 148: 2493-5

Muzzarelli R. A. A., Tanfani F., *Carbohydr. Polym.*, 1985, 5, 297.

Nicolosi R J, Wilson T A, Krause B R. 1998. Atherosclerosis 137: 77-85

Polnok A., et al., Eur. *J. Pharm. Biopharm.*, 2004, 57, 77-83.

Rünarsson Ö. V., et al., *Eur. Polym. J.*, 2007, 43, 2660-2671.

Sahni S., Chopra S., Ahmad F. J., Khar R. K., Journal of Pharmacy and Pharmacology, 2008, 60, 1111.

Sieval A. B., Thanou M., Kotzé A. F., Verhoef J. C., Brussee J., Junginger H. E., *Carbohydr. Polym.*, 1998, 36, 157-165.

Snyman D., Hamman J. H., Kotze J. S., Rollings J. E., Kotzé A. F., *Carbohydr. Polym.*, 2002, 50, 145-150.

Synman D., Hamman J. H., Kotzé A. F., *Drug Dev. Ind. Pharm.*, 2003, 29, 61.

Terpstra A H, Holmes J C, Nicolosi R J. 1991. The hypocholesterolemic effect of dietary soybean protein vs. casein in hamsters fed cholesterol-free or cholesterol-enriched semipurified diets. J Nutr 121: 944-7

Thanou M., Florea B. I., Langemeyer M. W. E., Verhoef J. C., Junginger H. E., *Pharm. Res.*, 2000, 17, 27.

Thanou M., Kotzé A. F., Scharringhausen T., Leuben H. L., De Boer A. G., Verhoef J. C., Junginger H. E., *J. Controlled Release*, 2000, 64, 15.

Thanou M., Verhoef J. C., Junginger H. E., *Adv. Drug Delivery Rev.*, 2001, 52, 117.

Thanou M., Verhoef J. C., Verheijden J. H. M., Junginger H. E., *Pharm. Res.*, 2001, 18, 823.

Thanou, M. et al. "Effect of N-trimethyl chitosan chloride, a novel absorption enhancer, on caco-2 intestinal epithelia and the ciliary beat frequency of chicken embryo trachea," Int. J. Pharm. Aug. 5, 1999; 185(1):73-82.

Thanou, M. et al. "Intestinal absorption of octreotide: N-trimethyl chitosan chloride (TMC) ameliorates the permeability and absorption properties of the somatostatin analogue in vitro and in vivo," J. Pharm. Sci. July 2000; 89(7):951-7.

Ueno, H. Adv. Drug Deliv. Rev., 2001, 52, 105-115.

Verheul, R. J., Biomaterials, 2008, 29, 3642-3649

Wilson T A, Nicolosi R J, Rogers E J, Sacchiero R, Goldberg D J. 1998. Studies of cholesterol and bile acid metabolism, and early atherogenesis in hamsters fed GT16-239, a novel bile acid sequestrant (BAS). Atherosclerosis 140: 315-24

CA 2507846.
CA 2507870.
CA 2580460.
CA 2623475.
CA 2631891.
EP 1250118B1.
U.S. Pat. No. 5,744,166.
U.S. Pat. No. 6,207,197.
U.S. Pat. No. 6,328,967.
U.S. Pat. No. 6,410,046.
U.S. Pat. No. 6,726,920.
U.S. Pat. No. 7,282,194.
U.S. Pat. No. 7,291,598.
U.S. Pat. No. 7,381,716.
U.S. Pat. No. 7,393,666.
U.S. Pat. No. 7,407,943.
U.S. Pat. No. 7,427,470.
U.S. Pat. No. 7,455,830.

The invention claimed is:

1. N,N,N-trimethylchitosan having a degree of quaternization, as measured in protonated form by $^1$H NMR spectroscopy, of 50% or more, degree of O-substitution of about 40% or less, and a molecular weight of about 50 kDa or more.

2. N,N,N-trimethylchitosan according to claim 1, having a degree of O-substitution of about 10% or less.

3. N,N,N-trimethylchitosan according to claim 2, having a degree of quaternization, as measured in protonated form by $^1$H NMR spectroscopy, of about 55% or more.

4. N,N,N-trimethylchitosan according to claim 3, having a degree of quaternization, as measured in protonated form by $^1$H NMR spectroscopy, of about 60% or more.

5. N,N,N-trimethylchitosan according to claim 4, having a degree of quaternization, as measured in protonated form by $^1$H NMR spectroscopy, of about 65% or more.

6. N,N,N-trimethylchitosan according to claim 1, having a degree of quaternization, as measured in protonated form and by $^1$H NMR spectroscopy, of about 75% or more.

7. A method of preparing the N,N,N trimethyichitosan of claim 1, the method comprising:
 a) providing chitosan;
 b) alkylating the chitosan via a reductive amination reaction performed using an aldehyde and formic acid to produce an N,N-dimethylchitosan, wherein substantially no N,N,N-trimethylchitosan is produced; and
 c) alkylating the N,N-dimethylchitosan using an alkylating agent and a base, in a reaction solvent comprising an organic solvent, water, and/or an alcohol to produce the N,N,N-trimethylchitosan, wherein the N,N,N-trimethylchitosan has a molecular weight of about 50 kDa or more, wherein about 40% or less of oxygen atoms that are unsubstituted in the chitosan are alkylated in the N,N,N-trimethylchitosan, and wherein 50% or more of nitrogen atoms are quaternized, as measured in protonated form by $^1$H NMR spectroscopy, in the N,N,N-trimethylchitosan.

8. A method according to claim 7, wherein the N,N-dimethylchitosan has a degree of N-substitution (N-DS) of about 2.0.

9. A method according to claim 7, wherein the chitosan has a degree of deacetylation (DD) of about 60% or more.

10. A method according to claim 7, wherein the alkylating agent is a haloalkane or a dialkylcarbonate.

11. A method according to claim 7, wherein the base is a hydroxide salt or an alkali carbonate or bicarbonate.

12. A method according to claim 7, wherein the reaction solvent is A N,N-dimethylformamide (DMF), water, an alcohol, a mixture of DMF and water, a mixture of DMF and an alcohol or a mixture of alcohols.

13. A method according to claim 7, wherein at least one of step b) and step c) is performed using a microwave.

14. A method according to claim 10, wherein the alkylating agent is iodomethane.

15. A method according to claim 11, wherein the base is sodium hydroxide or sodium carbonate.

16. A method according to claim 7, wherein the reaction solvent is water, an alcohol, or a mixture of water and an alcohol.

17. A method according to claim 16, wherein the reaction solvent is water together with up to 50% of an alcohol.

18. A method according to claim 17, where the reaction solvent is water together with about 10% methanol.

19. A method according to claim 7, further comprising a step of adding HCl, HBr, or HI to produce the N,N,N-trimethylchitosan with a chloride, a bromide or an iodide counterion.

\* \* \* \* \*